US010160972B2

(12) United States Patent
Copland, III et al.

(10) Patent No.: US 10,160,972 B2
(45) Date of Patent: Dec. 25, 2018

(54) METHODS AND MATERIALS FOR TREATING CANCER

(71) Applicant: Mayo Foundation for Medical Education and Research, Rochester, MN (US)

(72) Inventors: John A. Copland, III, Ponte Vedra Beach, FL (US); Laura Ann Marlow, Jacksonville, FL (US); Christina Von Roemeling, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/692,491

(22) Filed: Aug. 31, 2017

(65) Prior Publication Data
US 2017/0362595 A1 Dec. 21, 2017

Related U.S. Application Data

(63) Continuation of application No. 14/961,444, filed on Dec. 7, 2015, now abandoned, which is a continuation of application No. 14/383,385, filed as application No. PCT/US2013/029688 on Mar. 7, 2013, now Pat. No. 9,233,102.

(60) Provisional application No. 61/607,961, filed on Mar. 7, 2012.

(51) Int. Cl.
| A61K 48/00 | (2006.01) |
| C07H 21/02 | (2006.01) |
| C07H 21/04 | (2006.01) |
| C12N 15/113 | (2010.01) |
| G01N 33/574 | (2006.01) |
| A61K 31/4375 | (2006.01) |
| A61K 31/451 | (2006.01) |
| A61K 31/7088 | (2006.01) |

(52) U.S. Cl.
CPC ...... *C12N 15/1137* (2013.01); *A61K 31/4375* (2013.01); *A61K 31/451* (2013.01); *A61K 31/7088* (2013.01); *G01N 33/57407* (2013.01); *G01N 33/57438* (2013.01); *C12N 2310/11* (2013.01); *C12N 2310/531* (2013.01); *G01N 2800/52* (2013.01)

(58) Field of Classification Search
CPC ..... A61K 48/00; A61K 31/713; C12N 15/113
See application file for complete search history.

(56) References Cited

U.S. PATENT DOCUMENTS

| 7,547,698 | B2 | 6/2009 | Kamboj et al. |
| 7,592,343 | B2 | 9/2009 | Kamboj et al. |
| 7,767,677 | B2 | 8/2010 | Kamboj et al. |
| 7,893,066 | B2 | 2/2011 | Koltun et al. |
| 7,944,263 | B2 | 5/2011 | Suda |
| 7,960,358 | B2 | 6/2011 | Bhanot et al. |
| 8,017,761 | B2 | 9/2011 | McSwiggen et al. |
| 8,026,360 | B2 | 9/2011 | Kamboj et al. |
| 8,030,488 | B2 | 10/2011 | Sviridov et al. |
| 8,071,603 | B2 | 12/2011 | Kamboj et al. |
| 8,148,378 | B2 | 4/2012 | Gschwend et al. |
| 8,258,160 | B2 | 9/2012 | Dales et al. |
| 8,314,138 | B2 | 11/2012 | Dales et al. |
| 9,233,102 | B2 | 1/2016 | Copland, III et al. |
| 9,358,250 | B2 | 6/2016 | Ashkenazi |
| 2003/0064950 | A1 | 4/2003 | Ntambi et al. |
| 2005/0130193 | A1 | 6/2005 | Luxon et al. |
| 2008/0182851 | A1 | 7/2008 | Thomas et al. |
| 2010/0160323 | A1 | 6/2010 | Bischoff et al. |
| 2010/0249192 | A1 | 9/2010 | Li et al. |
| 2011/0021532 | A1 | 1/2011 | Powell et al. |
| 2011/0046134 | A1 | 2/2011 | Bischoff et al. |
| 2011/0166152 | A1 | 7/2011 | Leclerc et al. |
| 2011/0183958 | A1 | 7/2011 | Powell et al. |
| 2011/0213136 | A1 | 9/2011 | Bhanot et al. |
| 2011/0301143 | A1 | 12/2011 | Isabel et al. |
| 2012/0010186 | A1 | 1/2012 | Lachance et al. |
| 2012/0219623 | A1 | 8/2012 | Meinicke |

(Continued)

FOREIGN PATENT DOCUMENTS

| EP | 2266569 | 12/2010 |
| EP | 2269610 | 1/2011 |

(Continued)

OTHER PUBLICATIONS

"A Study to Assess the Safety and Efficacy of MK8245 in Patients With Type 2 Diabetes Mellitus and Inadequate Glycemic Control (MK8245-005 AM2)," ClinicalTrials.gov [online] Feb. 17, 2009 [retrived on Aug. 31, 2015]. Retrieved from the Internet <URL: https://www.clinicaltrials.gov/ct2/show/NCT00846391?term=mk-8245&rank=1>, 3 pages.

"A Study to Evaluate the Safety, Tolerability, Pharmacokinetics and Pharmacodynamics of MK8245 (8245-004)(Completed)," ClinicalTrials.gov [online] Nov. 7, 2008 [retrieved on Aug. 31, 2015]. Retrieved from the Internet: <https://www.clinicaltrials.gov/ct2/showNCT00790556?term=mk-8245&rank=3>, 3 pages.

"Compound Summary for CID 11973722," Pub Chem [online] created Jan. 3, 2007 [retrieved on Apr. 23, 2015]. Retrieved fmm the Internet: <URL: http://pubchem.ncbi.nlm.nih.gov/compound/11973722>, 13 pages.

(Continued)

*Primary Examiner* — Amy H Bowman
(74) *Attorney, Agent, or Firm* — Fish & Richardson P.C.

(57) ABSTRACT

This document provides methods and materials for treating cancers including renal cancer (e.g., renal cell carcinoma) as well as ovarian, breast, prostate, colon, pancreatic, bladder, liver, lung, and thyroid cancers and melanoma. For example, methods and material for using one or more inhibitors of an SCD1 polypeptide to treat renal cell carcinoma (e.g., clear cell renal cell carcinoma (ccRCC)) or to increase the efficacy of a renal cell carcinoma treatment are provided. In addition, this document provides methods and materials for using elevated SCD1 expression levels in diseased tissues as an indication that an SCD1 inhibitor can be used as an appropriate therapeutic to ameliorate the disease.

22 Claims, 32 Drawing Sheets

(56) References Cited

U.S. PATENT DOCUMENTS

| | | |
|---|---|---|
| 2012/0277280 A1 | 11/2012 | Li et al. |
| 2015/0045418 A1 | 2/2015 | Copland, III et al. |
| 2016/0152986 A1 | 6/2016 | Copland, III et al. |

FOREIGN PATENT DOCUMENTS

| | | |
|---|---|---|
| WO | WO 2006015621 | 2/2006 |
| WO | WO 2006034312 | 3/2006 |
| WO | WO 2006034338 | 3/2006 |
| WO | WO 2006034440 | 3/2006 |
| WO | WO 2006034441 | 3/2006 |
| WO | WO 2006101521 | 9/2006 |
| WO | WO 2006121250 | 11/2006 |
| WO | WO 2006130986 | 12/2006 |
| WO | WO 2007005763 | 1/2007 |
| WO | WO 2007009236 | 1/2007 |
| WO | WO 2007056846 | 5/2007 |
| WO | WO 2007071023 | 6/2007 |
| WO | WO 2007130075 | 11/2007 |
| WO | WO 2007134457 | 11/2007 |
| WO | WO 2007143823 | 12/2007 |
| WO | WO 2007143824 | 12/2007 |
| WO | WO 2008017161 | 2/2008 |
| WO | WO 2008020435 | 2/2008 |
| WO | WO 2008046226 | 4/2008 |
| WO | WO 2008064474 | 6/2008 |
| WO | WO 2008074824 | 6/2008 |
| WO | WO 2008074832 | 6/2008 |
| WO | WO 2008074834 | 6/2008 |
| WO | WO 2008089580 | 7/2008 |
| WO | WO 2009019566 | 2/2009 |
| WO | WO 2009060053 | 5/2009 |
| WO | WO 2009060054 | 5/2009 |
| WO | WO 2009106991 | 9/2009 |
| WO | WO 2009147125 | 12/2009 |
| WO | WO 2010025553 | 3/2010 |
| WO | WO 2010079197 | 7/2010 |
| WO | WO 2010086411 | 8/2010 |
| WO | WO 2010092163 | 8/2010 |
| WO | WO 2010094120 | 8/2010 |
| WO | WO 2010149640 | 12/2010 |
| WO | WO 2011011872 | 2/2011 |
| WO | WO 2011030312 | 3/2011 |
| WO | WO 2011064352 | 6/2011 |

OTHER PUBLICATIONS

"Pharmacokinetics and Pharmacodynamics of MK-8245 in Participants With Type 2 Diabetes (MK-8245-012)," ClinicalTrials.gov [online] Sep. 3, 2009 [retrieved on Aug. 31, 2015]. Retrieved from the Internet: <URL: https://www.clinicaltrials.gov/ct2/show/NCT00972322?term=mk-8245&rank=2>, 3 pages.

"SCD1 Inhibitor," BioVision [online] archived Sep. 24, 2013. Retrieved from the Internet:<URL: http://www.biovision.com/scd1-inhibitor-3983.html>, 1 page.

"Xenon and Novartis Sign Drug Development Deal for Obesity and Metabolic Disorders," PR Newswire [online] Sep. 20, 2004 [retrieved on Apr. 23, 2015]. Retrieved from the Internet: <URL: http://www.prnewswire.com/news-releases/xenon-and-novartis-sign-drug-development-deal-for-obesity-and-metabolic-disorders-73785902.html> 3 pages.

Berge et al., "Pharmaceutical Salts," *J. Pharm. Sci.*, 66(1): 1-19, Jan. 1977.

Chan, "Targeting the mammalian target of rapamycin (mTOR):a new approach to treating cancer," *Br J Cancer.* 91(8):1420-1424, Oct. 18, 2004.

Cohen et al., "Role for stearoyl-CoA desaturase-1 in leptin-mediated weight loss," *Science*, 297(5579):240-243, Jul. 12, 2002.

Cooper et al., "Reexpression of tumor suppressor, sFRP1, leads to antitumor synergy of combined HDAC and methyltransferase inhibitors in chemoresistant cancers," *Mol Cancer Ther.*, 11(10):2105-2115, Epub Jul. 23, 2012.

Copland et al., "Novel high-affinity PPARgamma agonist alone and in combination with paclitaxel inhibits human anaplastic thyroid carcinoma tumor growth via p21WAF1/CIP1," *Oncogene.*, 25(16):2304-2317, Apr. 13, 2006.

DiMauro et al., "Structural modifications of N-arylamide oxadiazoles: Identification of N-arylpiperidine oxadiazoles as potent and selective agonists of CB2," *Bioorg Med Chem Lett.*, 18(15):4267-4274, Epub Jul. 13, 2008.

Dobrzyn et al., "Loss of stearoyl-CoA desaturase 1 inhibits fatty acid oxidation and increases glucose utilization in the heart," *Am J Physiol Endocrinol Metab.*, 294(2):E357-E364, Epub Nov. 27, 2007.

Dondeti et al., "Integrative genomic analyses of sporadic clear cell renal cell carcinoma define disease subtypes and potential new therapeutic targets," *Cancer Res.*, 72(1):112-121, Epub Nov. 17, 2011.

Fritz et al., "Abrogation of de novo lipogenesis by stearoyl-CoA desaturase 1 inhibition interferes with oncogenic signaling and blocks prostate cancer progression in mice," *Mol Cancer Ther.*, 9(6):1740-1754, Epub Jun. 8, 2010.

GenBank® Accession No. AF097514.1 (GI No. 4808600), "*Homo sapiens* stearoyl-CoA desaturase (SCD) mRNA, complete cds," 3 pages, May 19, 1999.

GenPept. O00767 GI No. 21431730, "Acyl-CoA desaturase," Feb. 8, 2011, 6 pages.

Hess et al., "Inhibition of stearoylCoA desaturase activity blocks cell cycle progression and induces programmed cell death in lung cancer cells," *PLoS One.*, 5(6):e11394, 8 pages, Jun. 30, 2010.

Igal, "Stearoyl-CoA desaturase-1: a novel key player in the mechanisms of cell proliferation, programmed cell death and transformation to cancer," *Carcinogenesis.*, 31(9):1509-1515, Epub Jul. 1, 2010.

Issandou et al., "Pharmacological inhibition of stearoyl-CoA desaturase 1 improves insulin sensitivity in insulin-resistant rat models," *Eur J Pharmacol.*, 618(1-3):28-36, Epub Jul. 17, 2009.

Kim et al., "Identification of genes differentially expressed in the renal cell carcinoma by microarmy" *The Korean Society for Laboratory Medicine*, [author manuscript] 2009.

Kim et al., "Stearoyl CoA desaturase (SCD) facilitates proliferation of prostate cancer cells through enhancement of androgen receptor transactivation," *Mol Cells.*, 31(4):371-377, Epub Feb. 10, 2011.

Koltun et al., "Novel, potent, selective, and metabolically stable stearoyl-CoA desaturase (SCD) inhibitors," *Bioorg Med Chem Lett.*, 19(7):2048-2052, Epub Feb. 8, 2009.

Koltun et al., "Orally bioavailable, liver-selective stearoyl-CoA desaturase (SCD) inhibitors" *Bioorg Med Chem Lett.*, 19(11):3050-3053, Epub Apr. 8, 2009.

Koltun et al., "Potent, orally bioavailable, liver-selective stearoyl-CoA desaturase (SCD) inhibitors," *Bioorg Med Chem Lett.*, 19(15):4070-4074, Epub Jun. 13, 2009.

Leger et al., "Synthesis and biological activity of a potent and orally bioavailable SCD inhibitor (MF-438)," *Bioorg Med Chem Lett.*, 20(2):499-502, Epub Nov. 26, 2009.

Li et al., "Partial characterization of a cDNA for human stearoyl-CoA desaturase and changes in its mRNA expression in some normal and malignant tissues," *Int J Cancer.*, 57(3):348-352, May 1994.

Li et al., "Thiazole analog as stearoyl-CoA desaturase 1 inhibitor," *Bioorg Med Chem Lett.*, 19(17):5214-5217, Epub Jul. 9, 2009.

Liou et al., "Microarray gene expression profiling and analysis in renal cell carcinoma," *BMC Urol.*, 4:9, 11 pages, Jun. 22, 2004.

Liu et al., "Discovery of potent, selective, orally bioavailable stearoyl-CoA desaturase 1 inhibitors," *J Med Chem.*, 50(13):3086-3100. Epub May 27, 2007.

Liu, "Stearoyl-CoA desaturase inhibitors: update on patented compounds," *Expert Opin Ther Pat.*, 19(9):1169-1191, Sep. 2009.

Luyimbazi et al., "Rapamycin regulates stearoyl CoA desaturase 1 expression in breast cancer," *Mol Cancer Ther.*, 9(10):2770-2784, Epub Sep. 28, 2010.

Mason et al., "SCD1 inhibition causes cancer cell death by depleting mono-unsaturated fatty acids," *PLoS One.*, 7(3):e33823, Epub Mar. 22, 2012.

(56) References Cited

OTHER PUBLICATIONS

McAnuff et al., "Potency of siRNA versus snRNA mediated knockdown in vivo," *J Pharm Sci.*, 96(11):2922-2930, Nov. 2007.
Merck Sharp & Dohme Corp., "A Study to Evaluate the Safety, Tolerability, Pharmacokinetics and Pharmacodynamics of MK8245 (8245-004)(Completed)," ClinicalTrials.gov [online] Nov. 2014 [retrieved on Apr. 23, 2015]. Retrieved from the Internet: <URL: https://clinicaltrials.gov/ct2/show/results/NCT00790556>, 4 pages.
Minville-Walz et al., "Inhibition of stearoyl-CoA desaturase 1 expression induces CHOP-dependent cell death in human cancer cells," *PLoS One.*, 5(12):e14363, Dec. 16, 2010.
Miyazaki et al., "Hepatic stearoyl-CoA desaturase-1 deficiency protects mice from cathohydrate-induced adiposity and hepatic steatosis," *Cell Metab.*, 6(6):484-496, Dec. 2007.
Moore et al., "Loss of stearoyl-CoA desaturase expression is a frequent event in prostate carcinoma," *Int J Cancer.*, 114(4):563-571, Apr. 20, 2005.
Morgan-Lappe et al., "Identification of Ras-related nuclear protein, targeting protein for xenopus kinesin-like protein 2, and stearoyl-CoA desaturase 1 as promising cancer targets from an RNAi-based screen," *Cancer Res.*, 67(9):4390-4398, May 1, 2007.
Oballa et al., "Development of a liver-targeted stearoyl-CoA desaturase (SCD) inhibitor (MK-8245) to establish a therapeutic window for the treatment of diabetes and dyslipidemia," *J Med Chem.*, 54(14):5082-5096, Epub Jun. 28, 2011.
Powell et al "2-Aryl benzimidazoles. human SCD1-specific stearoyl coenzyme-A desaturase inhibitors," *Bioorg Med Chem Lett.*, 20(22):6366-6369. Epub Sep. 19, 2010.
Ramtohul et al., "Bicyclic heteroaryl inhibitors of stearoyl-CoA desaturase: from systemic to liver-targeting inhibitors," *Bioorg Med Chem Lett.*, 21(19):5692-5696, Epub Aug. 12, 2011.
Roongta et al., "Cancer cell dependence on unsaturated fatty acids implicates stearoyl-CoA desaturase as a target for cancer therapy," *Mol Cancer Res.*, 9(11):1551-1561, Epub Sep. 27, 2011.
RTT Staff Writer, "Merck Discontinues MK-3207 Clinical Development—Quick Facts," RTT News [online] Sep. 10, 2009 [retrieved on Apr. 23, 2015]. Retrieved from the Internet: <URL: http://www.rttnews.com/1062949/merck-discontinues-mk-3207-clinical-development-quick-facts.aspx>, 3 pages.
Scaglia et al., "Inhibition of stearoylCoA desaturase-1 inactivates acetyl-CoA carboxylase and impairs proliferation in cancer cells: role of AMPK," *PLoS One.*, 4(8):e6812, Aug. 27, 2009.
Schmittgen and Livak, "Analyzing real-time PCR data by the comparative C(T) method," *Nat Protoc.*, 3(6):1101-1108, 2008.
Tun et al., "Pathway signature and cellular differentiation in clear cell renal cell carcinoma " *PLoS One.*, 5(5):e10696, May 18, 2010.
Uto et al., "Discovery of novel SCD1 inhibitors: 5-alkyl-4,5-dihydro-3H-spiro[1,5-benzoxazepine-2,4'-piperidine] analogs," *Eur J Med Chem.*, 46(5):1892-1896, Epub Feb. 26, 2011.
Uto et al., "Novel benzoylpiperidine-based stearoyl-CoA desaturase-1 inhibitors: Identification of 6-[4-(2-methylbenzoyl)piperidin-1-yl]pyridazine-3-carboxylic acid (2-hydroxy-2-pyridin-3-ylethyl)amide and its plasma triglyceride-lowering effects in Zucker fatty rats," *Bioorg Med Chem Lett.*, 20(1):341-345, Epub Oct. 29, 2009.
Uto et al., "Synthesis and evaluation of novel stearoyl-CoA desaturase 1 inhibitors: 1'-{6-[5-(pyridin-3-ylmethyl)-1,3,4-oxadiazol-2-yl]pyridazin-3-yl}-3,4-dihydrospiro[chromene-2,4'-piperidine] analogs," *Eur J Med Chem.*, 45(11):4788-4796, Epub Aug. 4, 2010.
von Roemeling et al., "Aberrant lipid metabolism in anaplastic thyroid carcinoma reveals stearoyl CoA desaturase 1 as a novel therapeutic target," *J Clin Endocrinol Metab.*, 100(5):E697-709, Epub Feb. 12, 2015.
von Roemeling et al., "Stearoyl-CoA desaturase 1 is a novel molecular therapeutic target for clear cell renal cell carcinoma," *Clin Cancer Res.*, 19(9):2368-2380, Epub Apr. 30, 2013.
Xin et al., "Discovery of piperidine-aryl urea-based stearoyl-CoA desaturase 1 inhibitors " *Bioorg Med Chem Lett.*, 18(15):4298-4302, Epub Jun. 28, 2008.
Zhao et al., "Discovery of 1-(4-phenoxypipericlin-1-yl)-2-arylaminoethanone stearoyl-CoA desaturase 1 inhibitors," Bioorg Med Chem Lett., 17(12):3388-3391, Epub Apr. 5, 2007.
International Search Report and Written Opinion for International Application No. PCT/US2013/029688 dated Jul. 4, 2013, 8 pages.
International Preliminary Report on Patentability for International Application No. PCT/US2013/029688 dated Sep. 9, 2014, 6 pages.

FIG. 1B

| | Placebo | A939572 | Tem | Combo |
|---|---|---|---|---|
| Ki67 | 34.4% ± 2.6 | 29.3% ± 1.1 | 26.0% ± 2.1 | 24.7% ± 1.1 |
| CD31 | 139.5 ± 1.9 | 138.7 ± 2.0 | 137.0 ± 3.5 | 136.4 ± 2.3 |
| CC3 | 7.0% ± 1.3 | 10.3% ± 1.0 | 13.0% ± 1.9 | 18.5% ± 3.3 |
| P-mTOR | 121.7 ± 23.9 | 128.2 ± 17.5 | 76.2 ± 21.0 | 69.3 ± 24.6 |

FIG. 6B

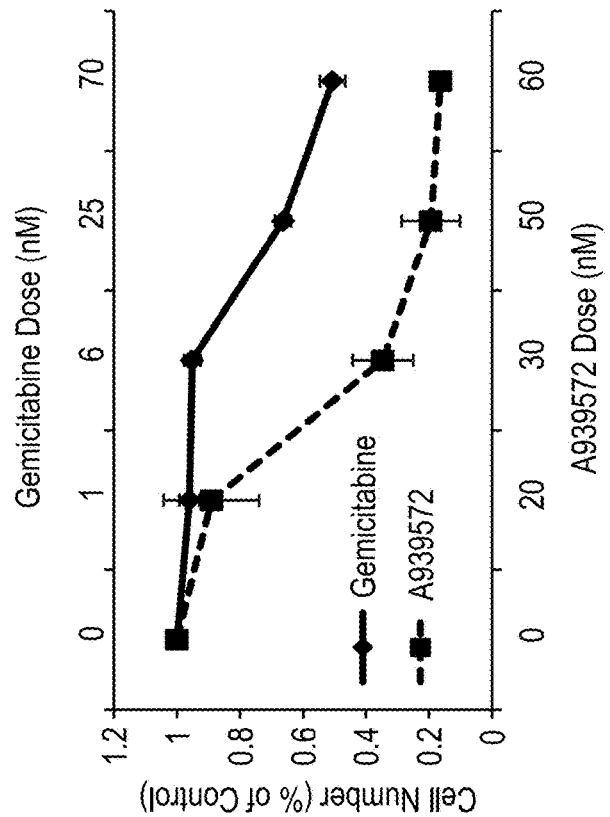
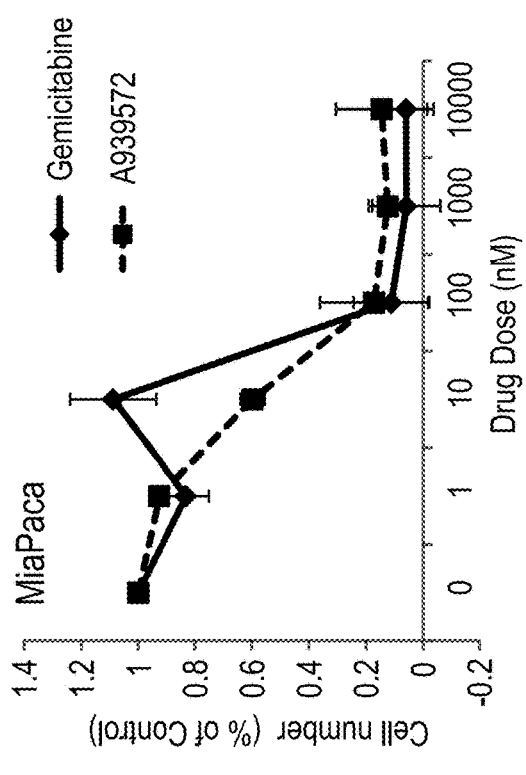
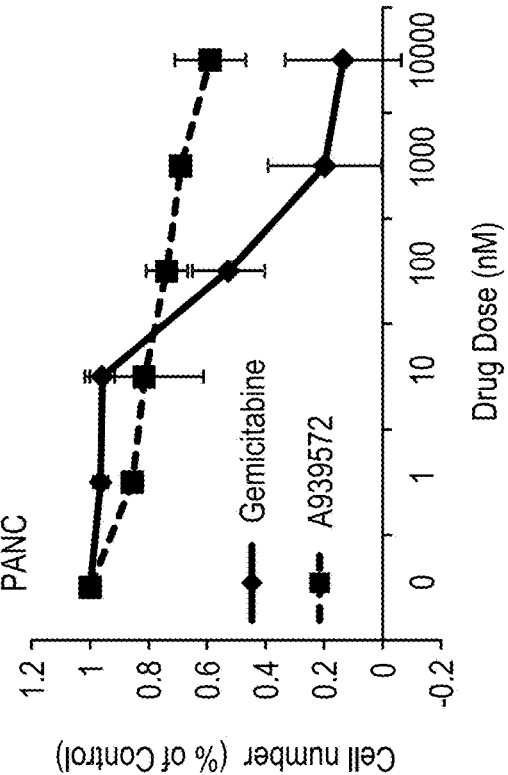
FIG. 7A
FIG. 7B
FIG. 7C

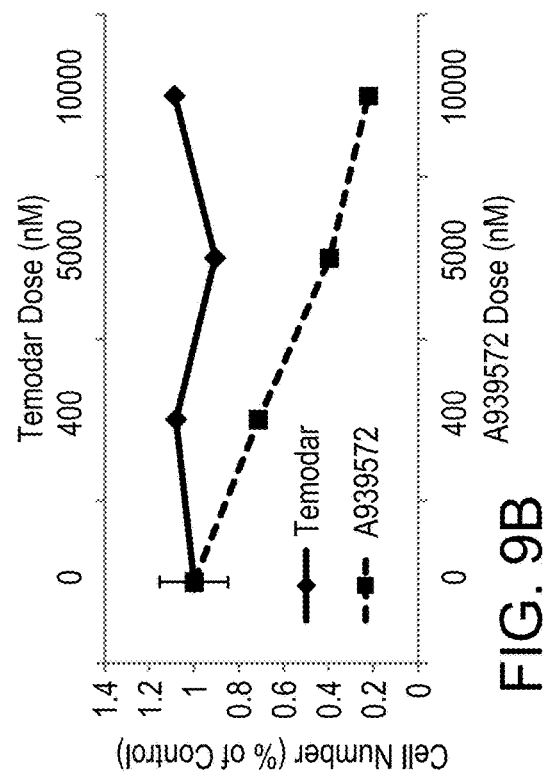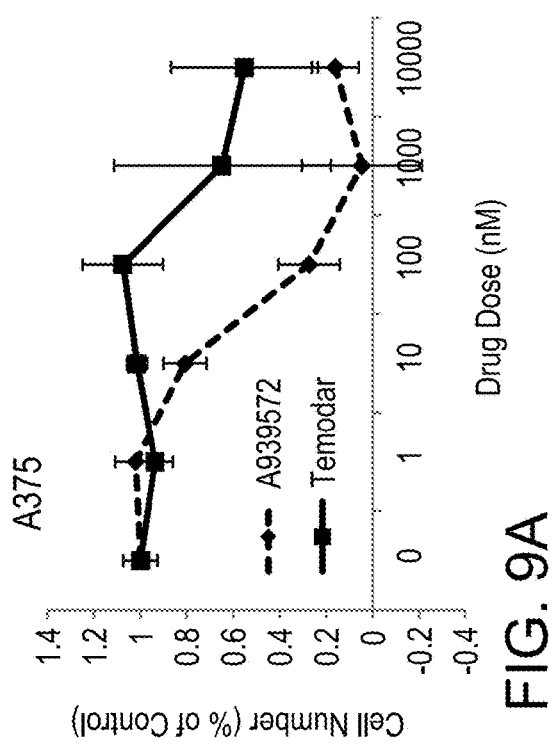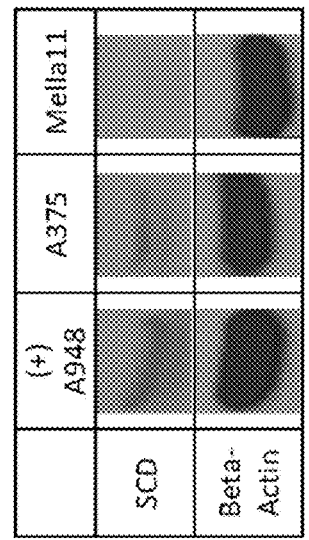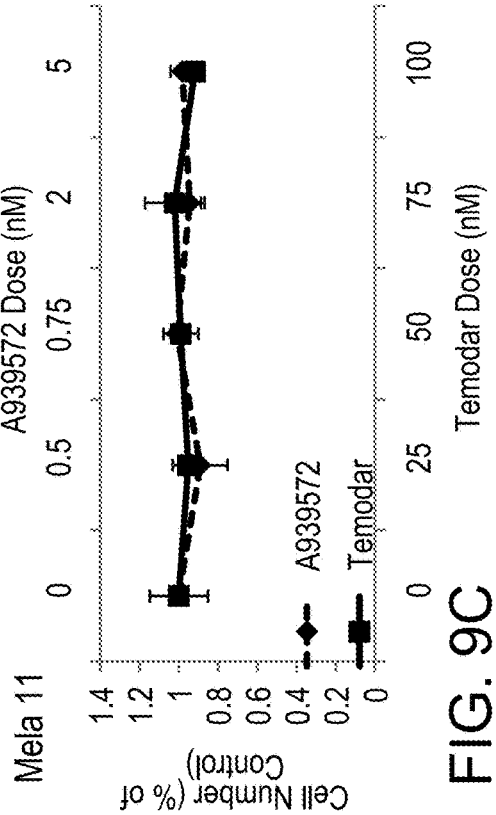
FIG. 9A
FIG. 9B
FIG. 9C
FIG. 9D

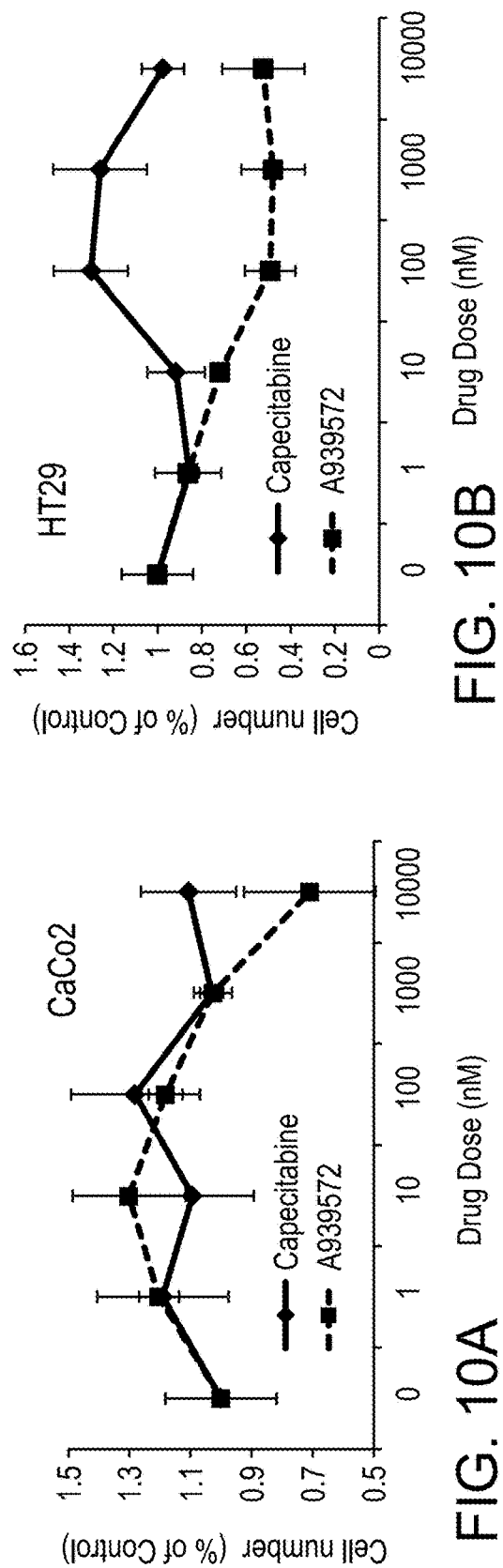
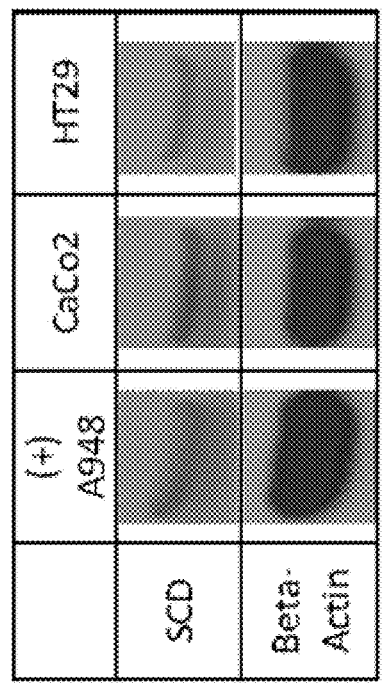
FIG. 10A
FIG. 10B
FIG. 10C

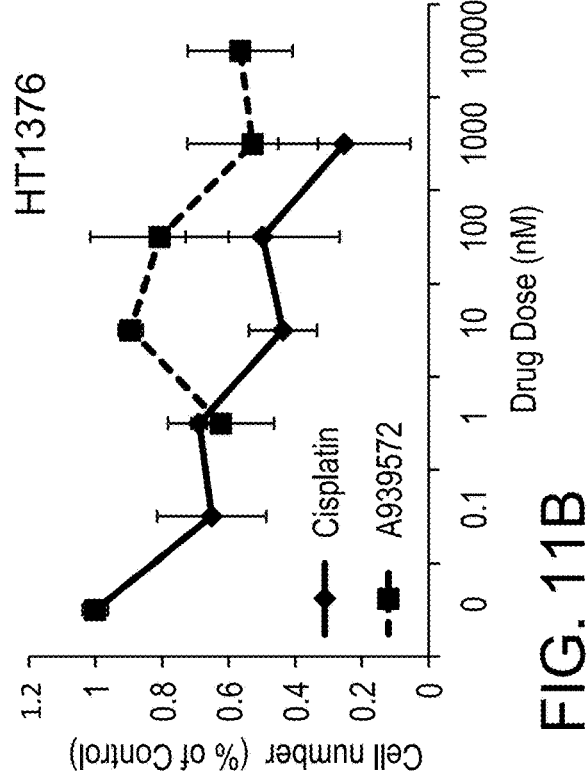
FIG. 11B
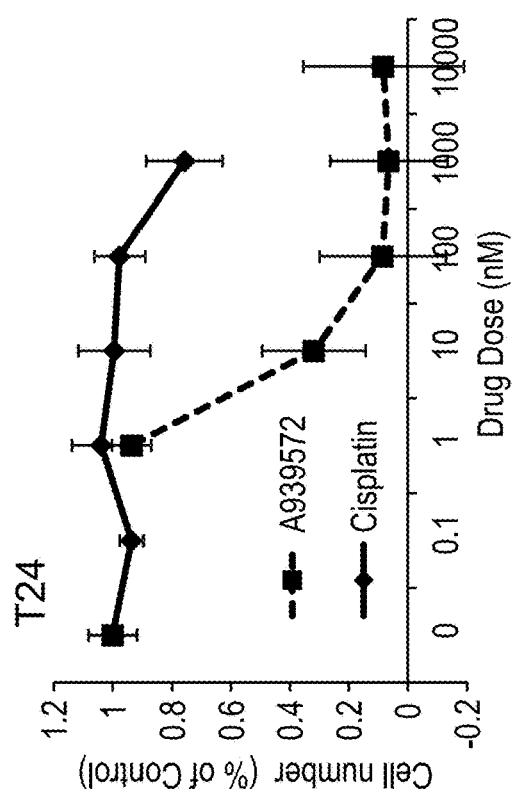
FIG. 11A
FIG. 11C

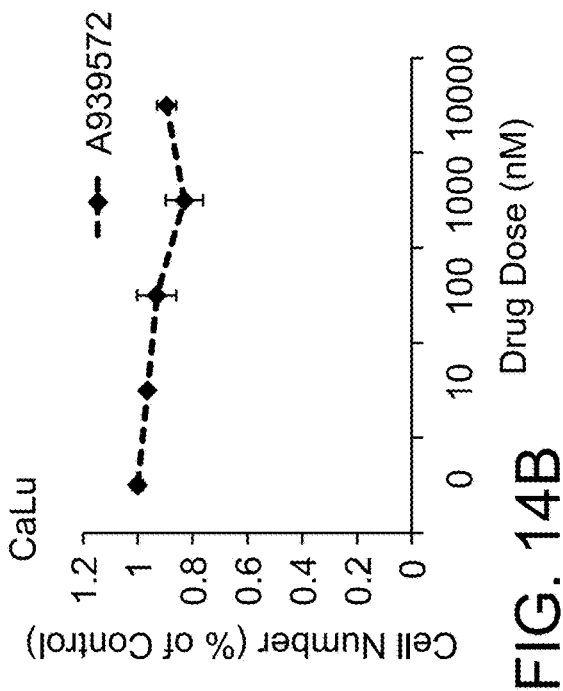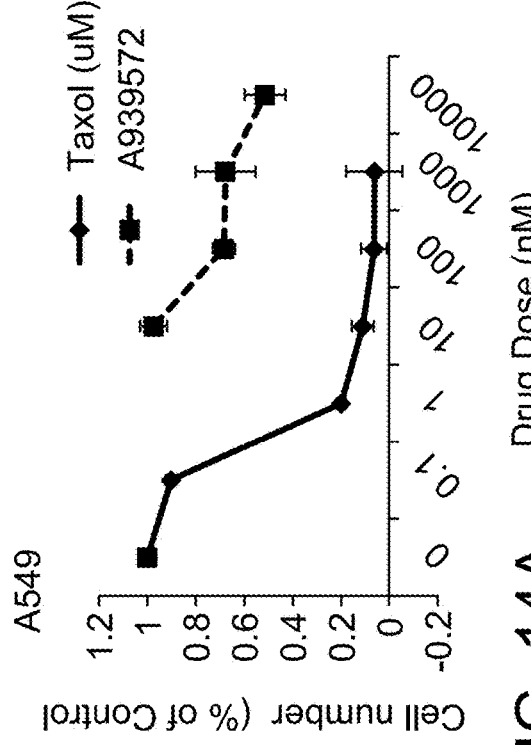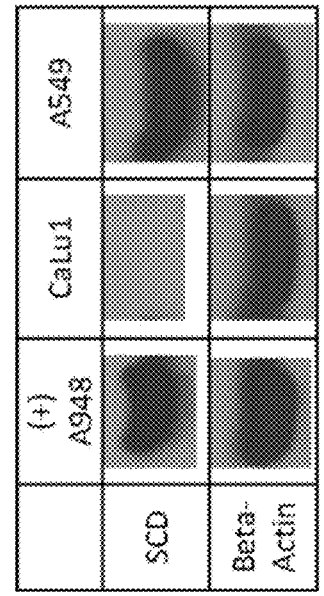
FIG. 14A
FIG. 14B
FIG. 14C

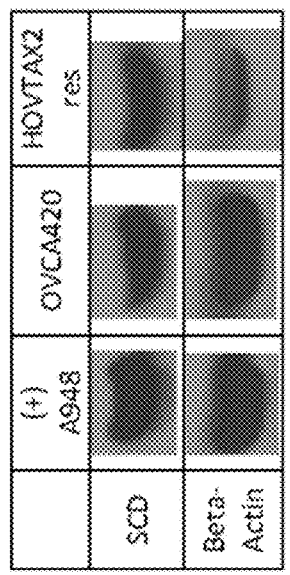
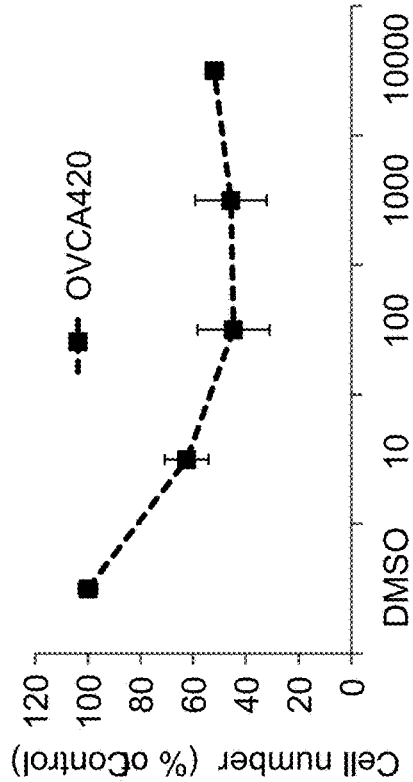
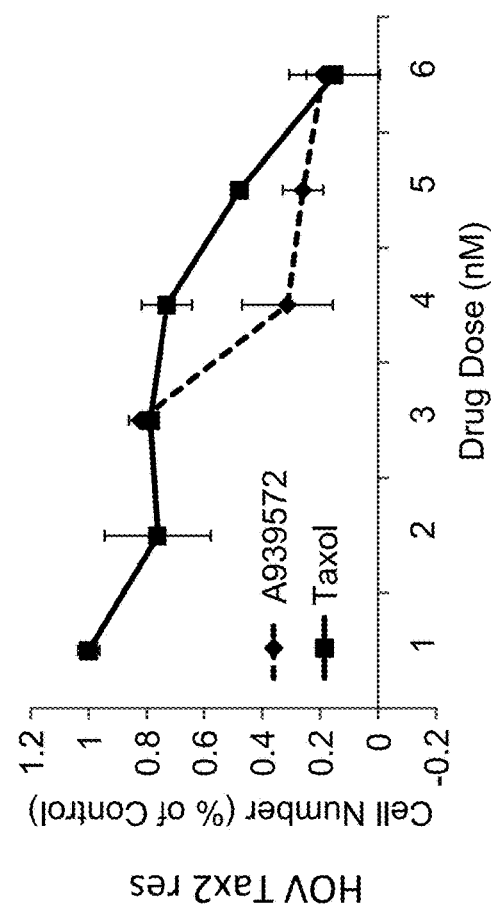
FIG. 15A
FIG. 15B
FIG. 15C

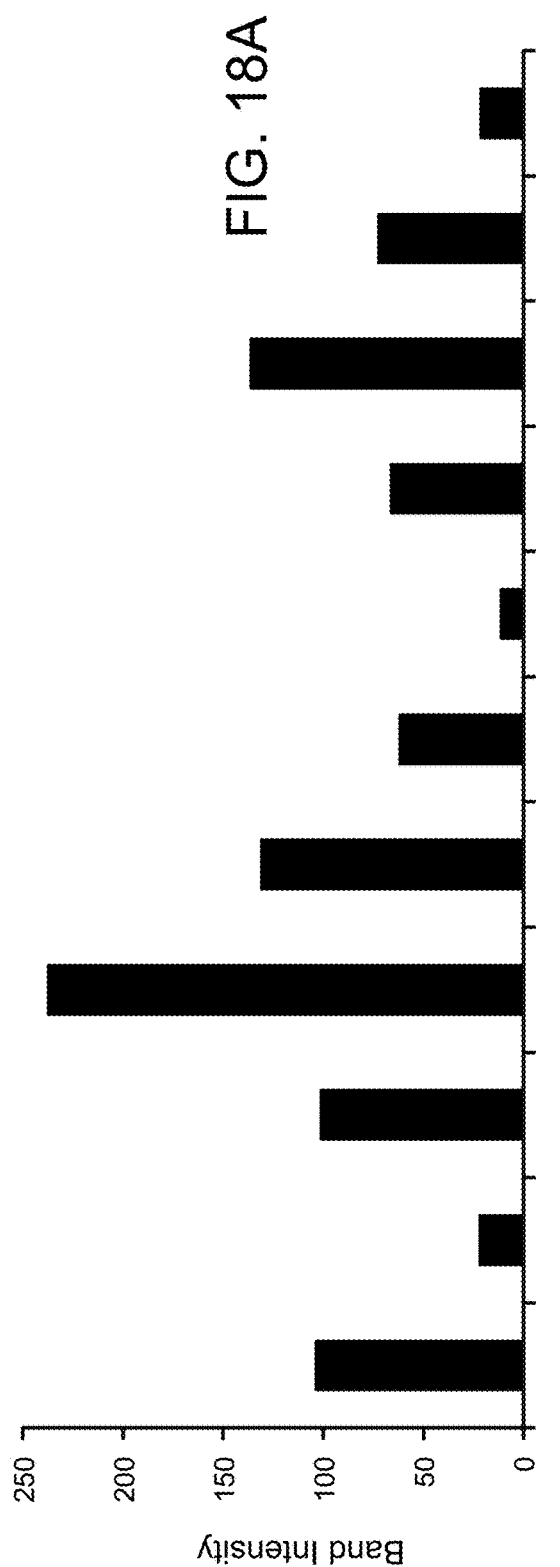
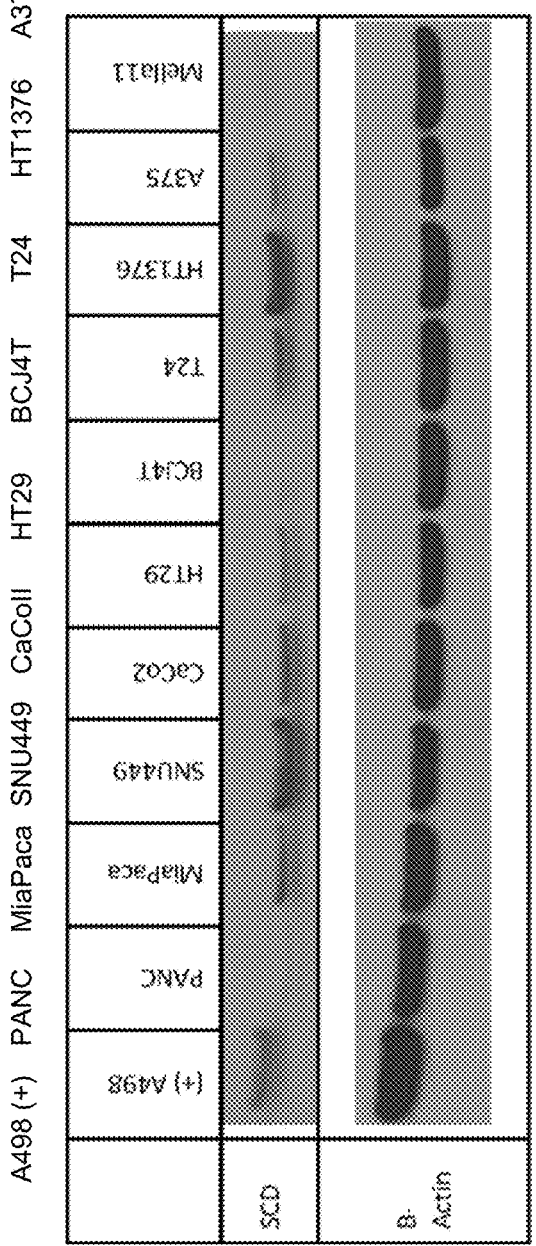

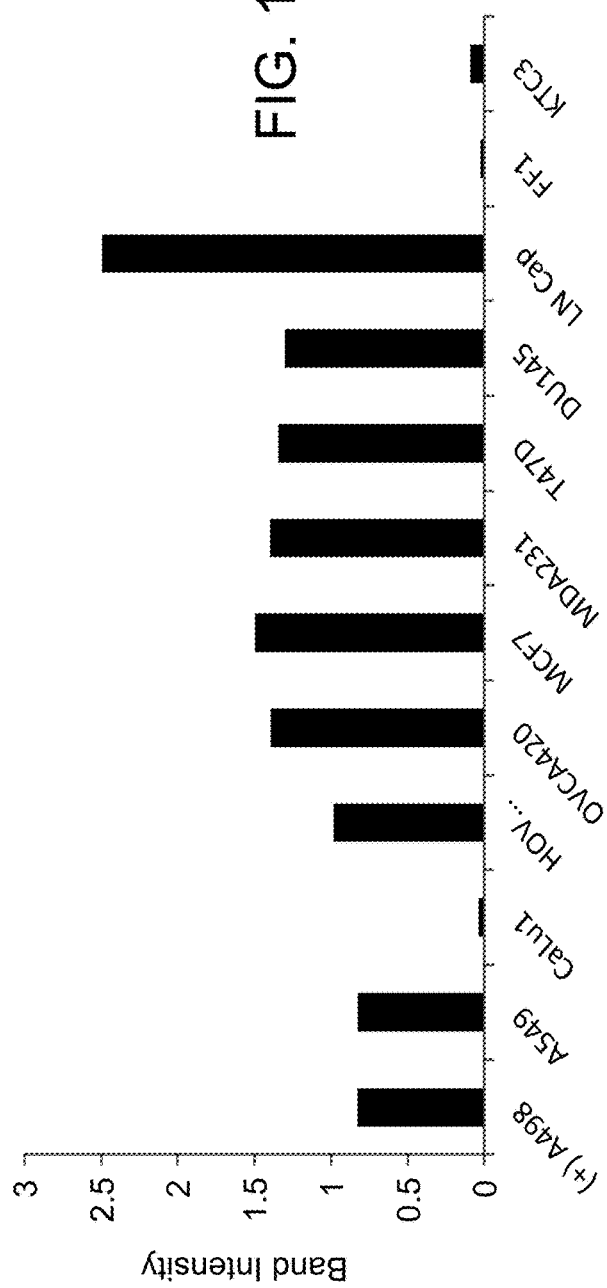
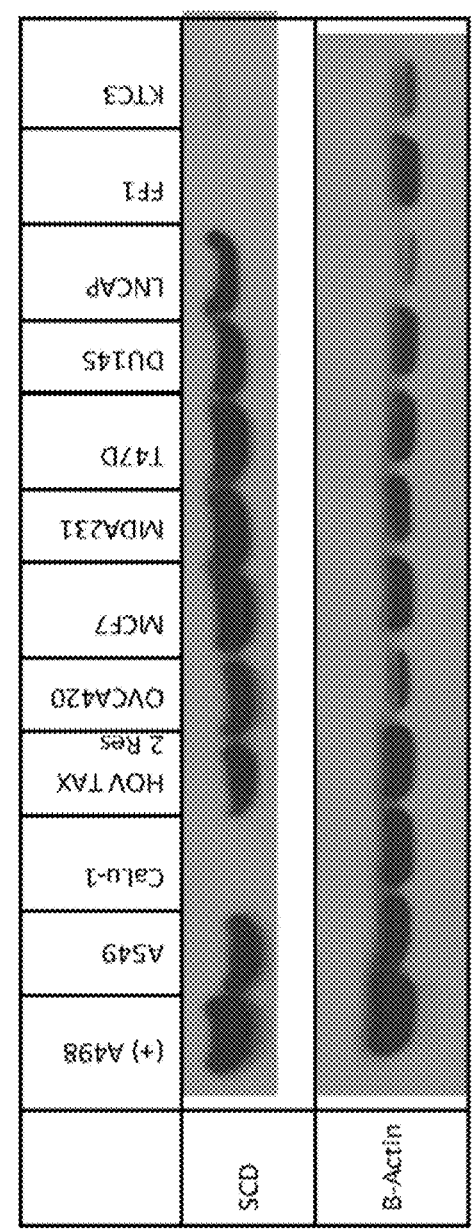

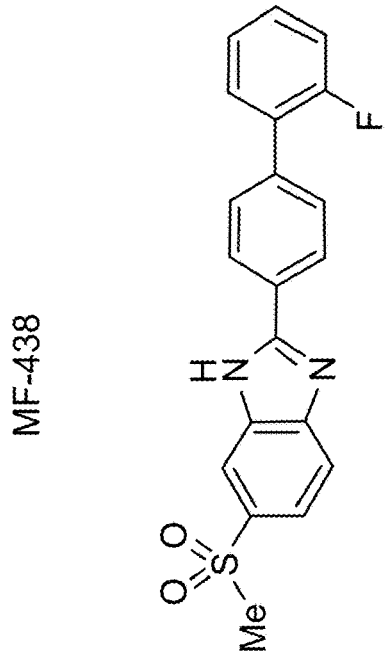
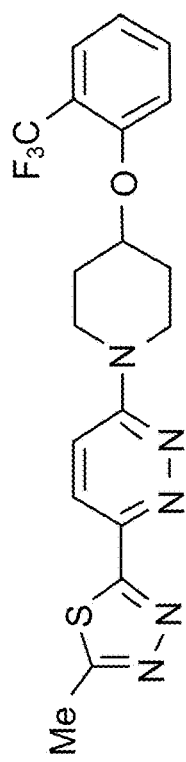
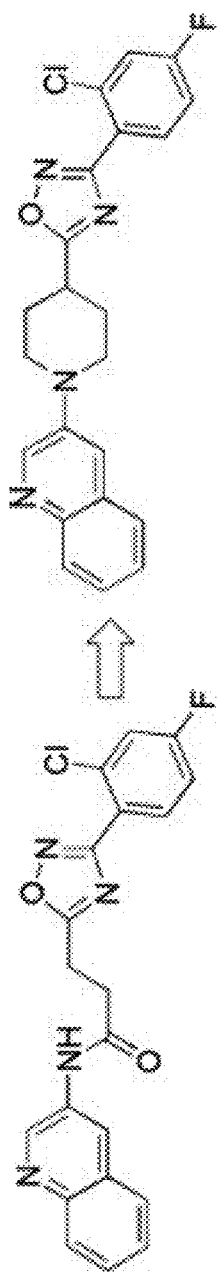
| No. | R | IC$_{50}$ (µM) |
|---|---|---|
| 7c | 2-Chlorophenoxyl | 0.051 ± 0.040 |
| 10a | Phenoxyl | 6.3 |
| 10b | 2-Bromophenoxyl | 0.058 ± 0.0007 |
| 10c | 2,5-Dichlorophenoxyl | 0.038 ± 0.017 |
| 10d | 2-Chloro-5-fluorophenoxyl | 0.051 ± 0.030 |
| 10e | 2,3-Difluorophenoxyl | 0.47 ± 0.18 |
| 10f | 2-Chloro-3,5-difluorophenoxyl | 0.035 ± 0.016 |
| 10g | 2-Trifluoromethyl-phenylamino | 0.10 ± 0.067 |
| 10h | Bz | >1 |
FIG. 21

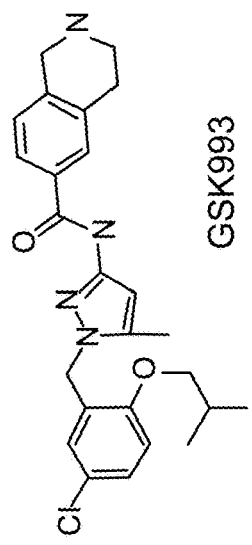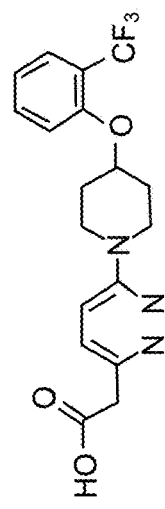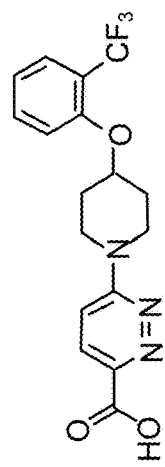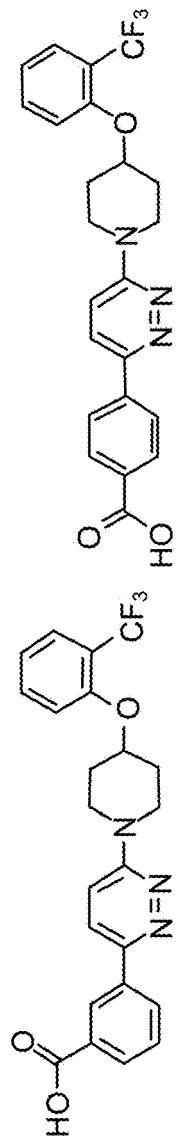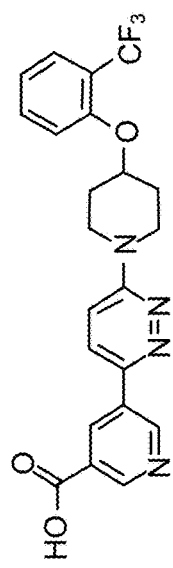
FIG. 22

METHODS AND MATERIALS FOR TREATING CANCER

CROSS-REFERENCE TO RELATED APPLICATIONS

This application is a continuation of U.S. application Ser. No. 14/961,444, filed Dec. 7, 2015 (now Abandoned), which is a continuation of U.S. application Ser. No. 14/383,385, filed Sep. 5, 2014 (now U.S. Pat. No. 9,233,102), which is a National Stage application under 35 U.S.C. § 371 of International Application No. PCT/US2013/029688, having an international filing date of Mar. 7, 2013, which claims priority to U.S. Provisional Application Ser. No. 61/607,961, filed on Mar. 7, 2012, which are incorporated by reference in their entirety herein.

STATEMENT AS TO FEDERALLY FUNDED RESEARCH

This invention was made with government support under CA104505 and CA136665 awarded by the National Institutes of Health. The government has certain rights in the invention.

BACKGROUND

1. Technical Field

This document relates to methods and materials involved in treating cancer, for example, renal cell carcinoma, ovarian, breast, prostate, colon, pancreatic, bladder, liver, lung, thyroid cancers, and melanoma. For example, this document provides methods and material for using one or more inhibitors of a stearoyl-Coenzyme A desaturase 1 (SCD1) polypeptide to treat cancer.

2. Background Information

The incidence and deaths caused by renal cell carcinoma are increasing in the United States. Indeed, mortality from renal cell carcinoma has increased over 37% since 1950.

SUMMARY

This document provides methods and materials for treating cancer, for example, renal cell carcinoma, ovarian, breast, prostate, colon, pancreatic, bladder, liver, lung, thyroid cancers, and melanoma. For example, this document provides methods and material for using one or more inhibitors of an SCD1 polypeptide to treat renal cell carcinoma (e.g., clear cell renal cell carcinoma (ccRCC)) or to increase the efficacy of a renal cell carcinoma treatment. As described herein, SCD1 polypeptides are overexpressed in certain cancer cells and are involved in the survival or proliferation of cancer cells. For example, reducing expression of renal cell carcinoma cells can result in reduced proliferation of renal cell carcinoma cells with minimal or no reduction in proliferation of normal kidney cells. In some cases, one or more inhibitors of an SCD1 polypeptide can be used to reduce the number of cancer cells within a mammal (e.g., a human). In some cases, one or more inhibitors of an SCD1 polypeptide can be used to increase the efficacy of a cancer treatment. For example, one or more inhibitors of an SCD1 polypeptide can be used to increase the efficacy of a renal cell carcinoma treatment (e.g., treatment with Nexavar®, Sutent®, Torisel®, Afinitor®, and interleukin-2).

In general, one aspect of this document features a method for reducing the number of renal cell carcinoma cells within a mammal. The method comprises, or consists essentially of, administering, to the mammal, an inhibitor of an SCD1 polypeptide under conditions wherein the number of viable renal cell carcinoma cells present within the mammal is reduced. The mammal can be a human. The administration can be an intratumoral, oral, intraperitoneal, intramuscular, or intravenous administration. The inhibitor can be A939572, MK-8245, CVT-11127, MF-152, or HYR-061. In another embodiment, one or more inhibitors of an SCD1 polypeptide can be administered with one or more inhibitors of a mTor polypeptide. Non-limiting examples of such inhibitors include sirolimus (RAPAMUNE®), temsirolimus (CCI-779), everolimus (RAD001), and ridaforolimus (AP-23573).

In another aspect, this document features a method for reducing the number of renal cell carcinoma cells within a mammal. The method comprises, or consists essentially of, administering, to the mammal, a composition under conditions wherein the number of viable renal cell carcinoma cells present within the mammal is reduced, wherein the composition comprises the ability to reduce SCD1 mRNA expression or SCD1 polypeptide expression. The mammal can be a human. The administration can be an intratumoral, oral, intraperitoneal, intramuscular, or intravenous administration. The composition can comprise a nucleic acid construct having the ability to express an shRNA directed against SCD1 nucleic acid.

In another aspect, this document features a method for reducing the number of cancer cells overexpressing an SCD1 polypeptide within a mammal. The method comprises, or consists essentially of, administering, to the mammal, an inhibitor of an SCD1 polypeptide under conditions wherein the number of viable cancer cells overexpressing an SCD1 polypeptide present within the mammal is reduced. Non-limiting examples of cancers include renal cell carcinoma, ovarian, breast, prostate, colon, pancreatic, bladder, liver, lung, thyroid cancers, and melanoma.

In another aspect, this document features a method for reducing the number of cancer cells overexpressing an SCD1 polypeptide within a mammal. The method comprises, or consists essentially of, administering, to the mammal, a composition under conditions wherein the number of viable cancer cells overexpressing an SCD1 polypeptide present within the mammal is reduced, wherein the composition comprises the ability to reduce SCD1 mRNA expression or SCD1 polypeptide expression. Non-limiting examples of cancers include renal cell carcinoma, ovarian, breast, prostate, colon, pancreatic, bladder, liver, lung, thyroid cancers, and melanoma.

In another aspect, this document features a method for identifying a mammal having cancer cells responsive to treatment with an inhibitor of an SCD1 polypeptide. The method comprises, or consists essentially of, (a) detecting the presence of cancer cells expressing an elevated level of an SCD1 mRNA or an SCD1 polypeptide, and (b) classifying the mammal has having cancer cells responsive to treatment with the inhibitor of an SCD1 polypeptide. The method can comprise measuring SCD1 mRNA expression using real time PCR. The method can comprise measuring SCD1 polypeptide expression using an immunohistochemical technique. The method can comprise measuring SCD1 polypeptide expression using a Western blot analysis. Non-limiting examples of cancers include renal cell carcinoma, ovarian, breast, prostate, colon, pancreatic, bladder, liver, lung, thyroid cancers, and melanoma.

In a further aspect, this document features a method for reducing the number of cancer cells within a mammal. The method comprises, or consists essentially of, administering, to said mammal, an inhibitor of an SCD1 polypeptide and an inhibitor of an mTor polypeptide under conditions wherein the number of viable cancer cells present within said mammal is reduced. In some cases, the inhibitor of an mTor polypeptide can be sirolimus (RAPAMUNE®), temsirolimus (CCI-779), everolimus (RAD001), or ridaforolimus (AP-23573). In certain cases, the mammal is a human. In some cases, the administration is an intratumoral, oral, intraperitoneal, intramuscular, or intravenous administration. In some cases, the inhibitor of an SCD1 polypeptide is A939572, MK-8245, CVT-11127, MF-152, or HYR-061. Non-limiting examples of cancer cells include one or more of ovarian cancer, breast cancer, prostate cancer, colon cancer, renal cancer, pancreatic cancer, bladder cancer, liver cancer, lung cancer, thyroid cancer, and melanoma.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1B contains photographs of representative ccRCC tissue and matched normal tissue stained for SCD1 polypeptide expression.

FIG. 2D contains photographs of an immunoblot for Poly-ADP ribose polymerase (PARP) cleavage and SCD1 expression in A498 and Caki1 cell lines.

FIG. 3A is a bar graph showing proliferation for SCD1 and PARP cleavage in Caki1 and A498 NT versus shSCD with or without OA-BSA supplementation. FIG. 3B contains photographs of a Western blot analysis for SCD1 and PARP cleavage in Caki1 and A498 NT versus shSCD with or without OA-BSA supplementation. FIG. 3C contains photographs of a phase-contrast microscopy representative ccRCC cell (Caki1) confluence at day 5 of proliferation assay with different treatment conditions.

FIG. 4A is a line graph showing cell proliferative response to dose out of A939572 in Caki1, A498, Caki2, and ACHN ccRCC cell lines. FIG. 4B is a bar graph displaying ccRCC proliferation rescue with OABSA in A939572 treated ccRCC cell lines. FIG. 4C contains photographs of a Western blot analysis for PARP cleavage in A939572 treated vs. control, as well as OA-BSA rescue in ccRCC cell lines. FIG. 4D contains representative phase contrast images of A939572 treated ccRCC cells (A498)+/− OA-BSA rescue at day 5.

FIG. 5A contains photographs of a Western blot analysis for expression of ER stress markers: BiP, CHOP, and spliced XBP1 in response to A939572 treatment or lentiviral silencing of SCD1 in Caki1 and A498. FIG. 5B provides bar graphs showing QPCR analysis of ER stress gene expression in Caki1 and A498 cells treated with A939572 or shSCD lentivirus+/−OA-BSA rescue. FIG. 5C provides bar graphs showing relative luciferase activity of ER stress p5xATF6-GL3 (UPR) luciferase reporter transfected in Caki1 and A498 cells treated with A939572 or shSCD lentivirus+/−OA-BSA supplementation.

FIGS. 6A-D. Treatment of ccRCC cells with SCD1 inhibitor in combination with the mTOR inhibitor Temsirolimus synergistically inhibits tumor cell growth in vivo. FIG. 6A is a line graph illustrating in vivo tumor growth analysis and animal weight of A498 ccRCC subcutaneous xenografts in female athymic nude mice treated with A939572 and Temsirolimus alone or in combination versus placebo control (n=10 per group). FIG. 6B contains photographs of IHC of tissue harvested from treatment groups stained for Ki67 and CC3 (quantitated by N-score), CD31 (quantitated by I-score), and phospho-mTOR (quantitated by H-score). Average group scores +/− the standard error are reported for each stain. FIG. 6C contains photographs of Western blot and quantitation of CHOP expression in all four treatment groups. FIG. 6D is an illustration of proposed SCD1 activity in ccRCC model: inhibition of SCD1 blocks desaturation of SFA resulting in an accumulation of SFA species which trigger the ER stress response.

FIGS. 7A-D are line graphs comparing cell number to dose of A939572 or Gemcitabine in MiaPaca and pancreatic cancer cells.

FIGS. 9A-C are line graphs comparing cell number to dose of A939572 or Temodar in A375 AND Mela 11 melanoma cancer cells. FIG. 9D contains photographs of Western Blot and quantitation of SCD1 and beta-actin expression.

FIGS. 10A-B are line graphs comparing cell number to dose of A939572 or Capecitabine in CaCo2 and HT29 colon cancer cells. FIG. 10C contains photographs of Western Blot and quantitation of SCD1 and beta-actin expression.

FIGS. 11A-B are line graphs comparing cell number to dose of A939572 or cisplatin in T24 and HT1276 bladder cancer cells. FIG. 11C contains photographs of Western Blot and quantitation of SCD1 and beta-actin expression.

FIGS. 14A-B are line graphs comparing cell number to dose of A939572 or Taxol in A549 and CaLu-1 lung cancer cells. FIG. 14C contains photographs of Western Blot and quantitation of SCD1 and beta-actin expression.

FIGS. 15A-B are line graphs comparing cell number to dose of A939572 or Taxol in OVCA420 and HOVTax2res ovarian cancer cells. FIG. 15C contains photographs of Western Blot and quantitation of SCD1 and beta-actin expression.

FIG. 18A is a bar graph illustrating SCD1 protein expression in various cancer cell lines. FIG. 18B contains photographs of Western Blot and quantitation of SCD1 and beta-actin expression.

FIG. 19A is a bar graph illustrating SCD1 protein expression in various cancer cell lines. FIG. 19B contains photographs of Western Blot and quantitation of SCD1 and beta-actin expression.

FIGS. 20-22 provide structures for exemplary SCD1 inhibitors.

DETAILED DESCRIPTION

Figure 1A:
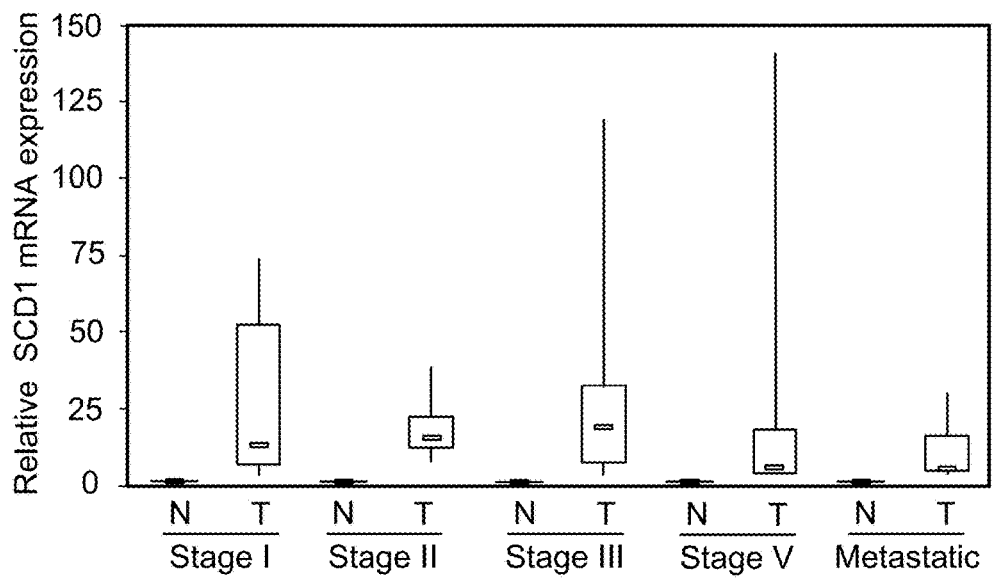
FIG. 1A is a graph plotting SCD1 mRNA levels in ccRCC tissue and matched normal tissue across stages I-IV.

This document provides methods and materials for treating cancer, for example, for example, renal cell carcinoma, ovarian, breast, prostate, colon, pancreatic, bladder, liver, lung, thyroid cancers, and melanoma. In some embodiments, this document provides methods and material for using one or more inhibitors of an SCD1 polypeptide to treat cancer (e.g., clear cell renal cell carcinoma (ccRCC)) or to increase the efficacy of a cancer treatment.

As described herein, one or more (e.g., one, two, three, four, or more) inhibitors of an SCD1 polypeptide can be administered to a mammal (e.g., a human) having cancer (e.g., renal cancer) under conditions wherein the number of cancer cells within the mammal is reduced. In some embodiments, one or more (e.g., one, two, three, four, or more) inhibitors of an SCD1 polypeptide can be administered to a mammal (e.g., a human) having renal cancer (e.g., ccRCC) under conditions wherein the number of renal cancer cells within the mammal is reduced.

An SCD1 polypeptide can be a human SCD1 polypeptide having the amino acid sequence set forth in GenBank® Accession No. 000767 (GI No. 21431730) or a human SCD1 polypeptide encoded by nucleic acid having the nucleic acid sequence set forth in GenBank® Accession No. AF097514.1 (GI No. 4808600). Examples of inhibitors of an SCD1 polypeptide include, without limitation, inhibitory anti-SCD1 polypeptide antibodies, siRNA molecules, shRNA molecules, nucleic acid vectors designed to express siRNA or shRNA molecules, anti-sense molecules, and small molecule antagonists such as A939572 (Biofine International Inc., Urvashi et al., *Mol. Cancer Res.*, 9:1551 (2011); Bristol-Myers Squibb R&D, Roongta et al., *Mol. Cancer Res.*, 9(11):1551-61 (2011)), MK-8245 (Merck Research Laboratories, Oballa et al., *J. Med. Chem.*, 54(14): 5082-96 (2011)), CVT-11127, MF-152 (Merck, Li et al., *Bioorganic & Medicinal Chemistry Letters*, 19:5214 (2009)), LCF369, CVT-11,563, CVT-12,012, DSR-4029, and GSK993 (Uto et al., *Eur. J. Med. Chem.*, 45:4788-4796 (2010)), MF-438 (Leger, S. et al., *Bioorg Med Chem Lett.* 20(2):499-502 (2010)), and HYR-061 (Medchem Express, Koltun et al., *Bioorganic & Medicinal Chemistry Letters*, 19(7):2048-2052 (2009), and Xin et al., *Bioorganic & Medicinal Chemistry Letters*, 18(15):4298-4302 (2008)). In some cases, an inhibitor of an SCD1 polypeptide can be an inhibitor described elsewhere (Igal, *Carcinogenesis*, 31(9): 1509-1515 (2010); Oballa, *J. Med. Chem.*, 54:5082-5096 (2011); Li et al., *Bioorganic & Medicinal Chemistry Letters*, 19:5214-5217 (2009); Uto et al., *Eur. J. Med. Chem.*, 46:1892-1896 (2011); Uto et al., *Eur. J. Med. Chem.*, 45:4788-4796 (2010); Liu, G. *Expert Opin Ter Pat*, 19(9): 1169-91 (2009); Powell, D. A., *Bioorg Med Chem Lett.* 20(22):6366-9 (2010), Mason P, et al., *PLoS ONE* 7(3): 33823 (2012), and Roongta et al., *Mol. Cancer Res.*, 9:1551-1561 (2011)).

Cancers that may be treated by an inhibitor of an SCD1 polypeptide, compositions and methods described herein include, but are not limited to, the following:

Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, epithelial cancer, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

In some cases, one or more (e.g., one, two, three, four, or more) inhibitors of an SCD1 polypeptide can be used as described herein to treat cancer, including renal cancer, ovarian, breast, prostate, colon, pancreatic, bladder, liver, lung, and thyroid cancers as well as melanoma.

For example, a human having cancer can be administered one or more inhibitors of an SCD1 polypeptide under conditions that result in reduced tumor size or stable disease. In some cases, one or more (e.g., one, two, three, four, or more) inhibitors of an SCD1 polypeptide can be used as described herein to increase the efficacy of a cancer treatment. In some embodiments (e.g., when compositions comprising one or more (e.g., one, two, three, four, or more) inhibitors of an SCD1 polypeptide are administered in conjunction with another anticancer agent), one can create a synergistic effect among the agents administered and thereby improve the outcome for a patient. In some embodiments, one or more (e.g., one, two, three, four, or more) inhibitors of an SCD1 polypeptide (or a pharmaceutically acceptable salt form thereof) can be administered in combination with (i.e., before, during, or after) administration of a pain relief agent (e.g., a nonsteroidal anti-inflammatory drug such as celecoxib or rofecoxib), an antinausea agent, or an additional anticancer agent (e.g., paclitaxel, docetaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, herceptin, avastin, cytarabine, dactinomycin, interferon alpha, streptozocin, prednisolone, irinotecan, sulindac, 5-fluorouracil, capecitabine, oxaliplatin/5 FU, abiraterone, letrozole, 5aza/romidepsin, or procarbazine). In certain embodiments, the anticancer agent is paclitaxel or docetaxel. In other embodiments, the anticancer agent is cisplatin or irinotecan.

For example, a human having ccRCC can be administered one or more inhibitors of an SCD1 polypeptide under conditions that result in reduced tumor size or stable disease. In some cases, one or more (e.g., one, two, three, four, or more) inhibitors of an SCD1 polypeptide can be used as described herein to increase the efficacy of a renal cell carcinoma treatment. Examples of such renal cell carcinoma treatments include, without limitation, treatment with Nexavar®, Sutent®, Torisel®, Afinitor®, or interleukin-2.

In some cases, one or more (e.g., one, two, three, four, or more) inhibitors of an SCD1 polypeptide can be used as described herein can be used in combination with one or more (e.g., one, two, three, four, or more) inhibitors of mammalian target of rapamycin (mTor) polypeptide. Non-limiting examples of mTor inhibitors include: sirolimus (RAPAMUNE®), temsirolimus (CCI-779), everolimus (RAD001), ridaforolimus (AP-23573).

Accordingly, provided herein is a method for reducing the number of cancer cells within a mammal, wherein the method comprises administering, to the mammal, an inhibitor of an SCD1 polypeptide and an inhibitor of an mTor polypeptide under conditions wherein the number of viable cancer cells present within said mammal is reduced. In some embodiments, the one or more mTor inhibitor can include a standard of care drug for a particular cancer cell type. For example, an SCD1 inhibitor can be administered with paclitaxel and/or platin (cisplatin, carboplatin, or oxaliplatin) for the treatment of ovarian cancer. In some embodiments, the following standard of care drugs can be combined with an SCD1 inhibitor for the following cancers:

Lung—paclitaxel
Colon—capecitabine
Breast
Metastatic breast—capecitabine, paclitaxel, and/or gemcitabine
Hormonally responsive breast—aromatase inhibitors such as letrazole and/or antiestrogens such as tamoxifen
HER2 positive—Herceptin
Melanoma—temodar, and/or BRAF inhibitors
Prostate—abiraterone
Bladder—gemcitabine and/or paclitaxel
Thyroid—paclitaxel and/or cisplatin
Pancreatic—gemcitabine
Liver—sorafanib In some embodiments, the combination of one or more inhibitors of an SCD1 polypeptide and one or more inhibitors of mTor exhibit a synergistic response. In some embodiments, the one or more inhibitors of an SCD1 polypeptide can be administered before, during, or after administration of the one or more inhibitors of mTor.

An inhibitor of an SCD1 polypeptide can also be administered to a subject in combination with surgical methods to treat cancers, e.g., resection of tumors. The inhibitor can be administered to the individual prior to, during, or after the surgery. The inhibitor can be administered parenterally, intravenous or injected into the tumor or surrounding area after tumor removal.

Typically, one or more of the inhibitors of an SCD1 polypeptide provided herein can be formulated into a pharmaceutical composition that can be administered to a mammal (e.g., rat, dog, horse, cat, mouse, rabbit, pig, cow, monkey, or human). For example, A939572 or a pharmaceutically acceptable salt thereof can be in a pharmaceutically acceptable carrier or diluent. A "pharmaceutically acceptable carrier" refers to any pharmaceutically acceptable solvent, suspending agent, or other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, without limitation, water, saline solutions, dimethyl sulfoxide, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate).

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The invention will be further described in the following examples, which do not limit the scope of the invention described in the claims.

EXAMPLES

General Materials and Methods
Cell Culture ccRCC cell lines: RWV366T and KIJ265T (16) (both stage IV ccRCC patient tissue derived), A498, Caki1, Caki2, and ACHN (ATCC) and K347N, K355N, K359N, K360N, K365N, and K366N normal renal tissue derived mortal cells (NRE) were cultured in DMEM medium (Cellgro) containing 5% FBS (Hyclone) and 1× penicillin-streptomycin (Invitrogen) at 37° C. in humidified conditions with 5% $CO_2$.
Proliferation, Treatment, and Rescue Assays Cells were plated (0.5 or $1 \times 10^5$/well) in 24-well plates for proliferation or treatment assays, in triplicate. Cells were trypsinized (0.25%) and counted using a Coulter Particle Counter at specified time intervals. For SCD1 rescue assays, oleic acid-albumin was added to media at 5 µM. Drug stocks were prepared in DMSO. Monotherapeutic treatment identified drug dose-response. Combinatorial dosing ranged up to the IC50 for each inhibitor. Temsirolimus dosing was performed as described in the text. Soft agar cultures were prepared by diluting 2× growth medium 1:1 in 1.5% Seaplaque®GTG® agarose, with 500 cells/plate in 60 mm culture dishes. Colonies were stained with Giemsa (LabChem Inc.) and counted after 3 wks. Cell images were obtained with an OlympusIX71 microscope at 20× magnification.
Lentivirus MISSION shRNA pLK0.1 constructs were used to make self-inactivating shRNA lentiviruses for human SCD1 (clones: NM_005063.3-1200s1c1[shSCD1200], NM_005063.3-780s1c1[shSCD780]), and a non-target (NT) random scrambled sequence control (SHC002). Transfection reagents Lipofectamine 2000 and ViraPower were used to generate lentiviruses using HEK293FT viral progenitor cells. ccRCC and NRE cells were incubated with lentivirus plus 5 µg/mL polybrene for 24 hrs prior to clonal selection with Puromycin.
Transfections and Luciferase Assays For transient transfection, Caki1 and A498 cells were transfected using Lipofectamine 2000. Cells treated with DMSO vs. A939572 or infected using shSCD780 lentiviral constructs vs. NT control were harvested after 48 hrs using Promega's Dual Luciferase assay kit per the manufacturer's protocol and luciferase activity was measured using a Veritas Luminometer; reported as relative luminescence.
RNA Isolation and Quantitative PCR An RNAqueous Midi Kit was utilized to extract and purify RNA from cell lines. Human tissue RNA was prepared using TRIzol® per manufacturer's protocol followed by purification using the RNAqueous Midi Kit. The O.D. 260/280 ratio of the mRNA was at least 1.8 and the 18s/28s bands were verified on a 1% agarose gel. cDNA was prepared from purified RNA samples using High Capacity cDNA Reverse Transcriptase Kit per manufacturer's instruction. TaqMan®Fast Universal PCR Master Mix and TaqMan®FAMTM dye-labeled probes including POLR2A (Hs00172187_m1) (normalization control), SCD1 (Hs01682761_m1), HSPA5 (Hs99999174_m1), CEBPβ (CEBPB Hs00270923_s1), GADD45A (Hs00169255_m1), DDIT3 (Hs01090850_m1), and HERPUD1 (Hs01124269_m1) were combined with prepared cDNA samples to analyze relative mRNA expression via qPCR. Fold change values were compared between normal and tumor, non-target scrambled lentiviral and target lentiviral infected, and DMSO vs. A939572 treated samples using the ΔΔCt method (Schmittgen T D, Livak K J. Analyzing real-time PCR data by the comparative C(T) method. *Nat Protoc.* 2008; 3:1101-8).
Gene Array Expression Analysis Gene array expression analysis was performed using Affymetrix Human Genome U133 Plus 2.0 Array chip. The details of the data processing and methodology were previously described in (Tun H W, Marlow L A, von Roemeling C A, Cooper S J, Kreinest P, Wu K, et al. Pathway signature and cellular differentiation in clear cell renal cell carcinoma. *PLoS One.* 2010; 5:e10696). Gene expression data was deposited at Gene Expression Omnibus (Accession#GSE41485). Pathway analysis was performed using IPA (Ingenuity® Systems).
Western Blot Analysis Protein extracts, electrophoresis, and membrane transfers were prepared as previously described (Copland J A, Marlow L A, Kurakata S, Fujiwara K, Wong A K, Kreinest P A, et al. Novel highaffinity PPARgamma agonist alone and in combination with paclitaxel inhibits human anaplastic thyroid carcinoma tumor growth via p21WAF1/CIP1. *Oncogene.* 2006; 25:2304-17). Primary antibodies included SCD1, PARP, DDIT3, BiP, sXBP1, and β-actin. A Supersignal chemiluminescent kit was used to perform detection.
IHC and ICC Analysis Formalin fixed, paraffin-embedded tissue microarray (TMA) of patient ccRCC tumor and matched normal tissues and TMA of combinatorial in vivo mouse tumor tissue. The TMAs were mounted on slides from paraffin-embedded blocks according to IHC procedure and samples were blocked with Diluent that contained Background Reducing Components (Dakocytomation) for 30 min and then probed for SCD1, Ki67, Caspase-3, CD31, phospho-mTOR, DDIT3, and XBP1. ICC preparation and staining was performed as previously described (Cooper S J, Von Roemeling C A, Kang K H, Marlow L A, Grebe S K, Menefee M E, et al. Reexpression of tumor suppressor, sFRP1, leads to antitumor synergy of combined HDAC and methyltransferase inhibitors in Chemoresistant cancers. *Mol Cancer Ther.* 2012). Stain scoring was done using algorithms generated with Imagescope software created by a histologist. H-scores were calculated based upon signal intensity (0-3+) using the formula: $[(1+\%\times1)+(2+\%\times2)+(3+\%\times3)]$, intensity (I)-scores were calculated by dividing signal intensity by area, and nuclear (N)-scores were calculated by dividing % positive nuclei by total nuclei examined per area. Cases where insufficient tumor tissue presented were excluded from the study. 20× images were obtained using Scanscope XT and Imagescope software. RWV366T cell line validation was carried out as previously described (Cooper S J, Von Roemeling C A, Kang K H, Marlow L A, Grebe S K, Menefee M E, et al. Reexpression of tumor suppressor, sFRP1, leads to antitumor synergy of combined HDAC and methyltransferase inhibitors in chemoresistant cancers. *Mol Cancer Ther.* 2012).

In Vivo Analysis

A498 cells were subcutaneously implanted in athymic nu/nu mice at $1\times10^6$ cells/mouse in 50% Matrigel. Tumors reached ~50 mm$^3$ prior to treatment, which was carried out for 4 wks. A939572 was administered via oral feeding using strawberry flavored Kool-Aid® in sterilized $H_2O$ (0.2 g/mL) vehicle at 30 mg/kg in a 50 µl dose twice daily/mouse. Temsirolimus was solubilized in 30% ethanol/saline and administered via intraperitoneal injection at 10 mg/kg in a 50 µl dose once every 72 hrs/mouse. Tumor volumes were calculated using the formula 0.5236(L*W*H) and body weight were measured every 3 days.

DNA Isolation and STR Analysis

Genomic DNA was extracted from both RWV366T patient primary tissue and matching cell line using Purelink™ Genomic DNA mini kit. Sixteen STR markers were PCR amplified using fluorescently labeled primers from ABI, and were analyzed using ABI 3130. Peak sizes were calculated versus a co-injected size standard using Gene Marker.

Statistical Analysis

Data values are presented as either percentage or fold change ±s.d. unless otherwise specified. Fold change values 1.5< are considered statistically significant. Treatment group comparisons were analyzed using two-tailed paired Student's t-test with $p<0.05$ being considered statistically significant. Statistically significant results are indicated by asterisk (*). Drug synergy statistics are indicated via combination index (CI) determined using CalcuSyn® as described in the text.

Example 1

SCD1 Polypeptide is Upregulated in ccRCC and is Involved in Tumor Cell Survival

Normal kidney tissue and matched ccRCC tissue samples were obtained, and the levels of SCD1 mRNA and SCD1 polypeptide expression were determined. SCD1 mRNA levels and SCD1 polypeptide levels were elevated in matched ccRCC samples when compared to normal samples (FIGS. 1A and 1B).

Figure 1C:
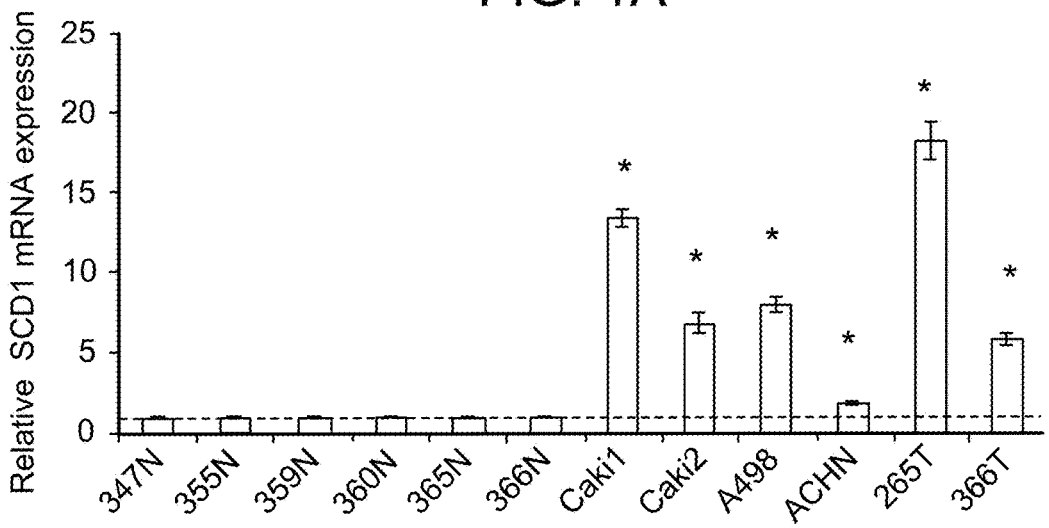
FIG. 1C is a graph plotting SCD1 mRNA levels in normal renal epithelial cell lines (347N, 355N, 359N, 360N, 365N, and 366N) versus ccRCC cell lines.
Figure 1D:
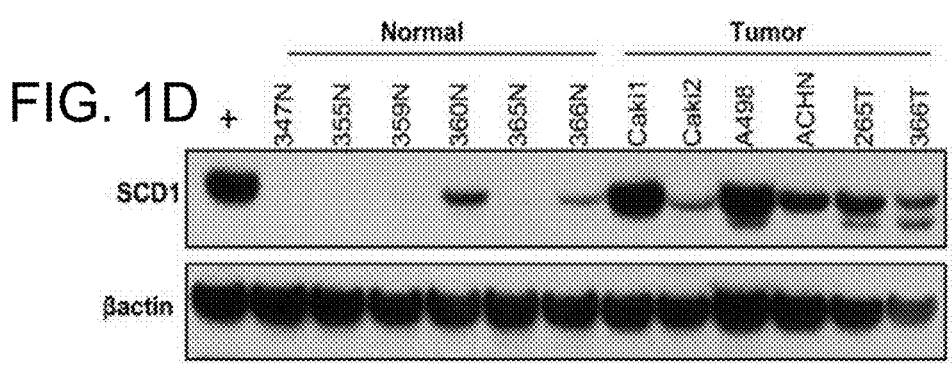
FIG. 1D contains photographs of a Western blot analysis of SCD1 polypeptide expression by normal cell lines and ccRCC cell lines.
Figure 1B:
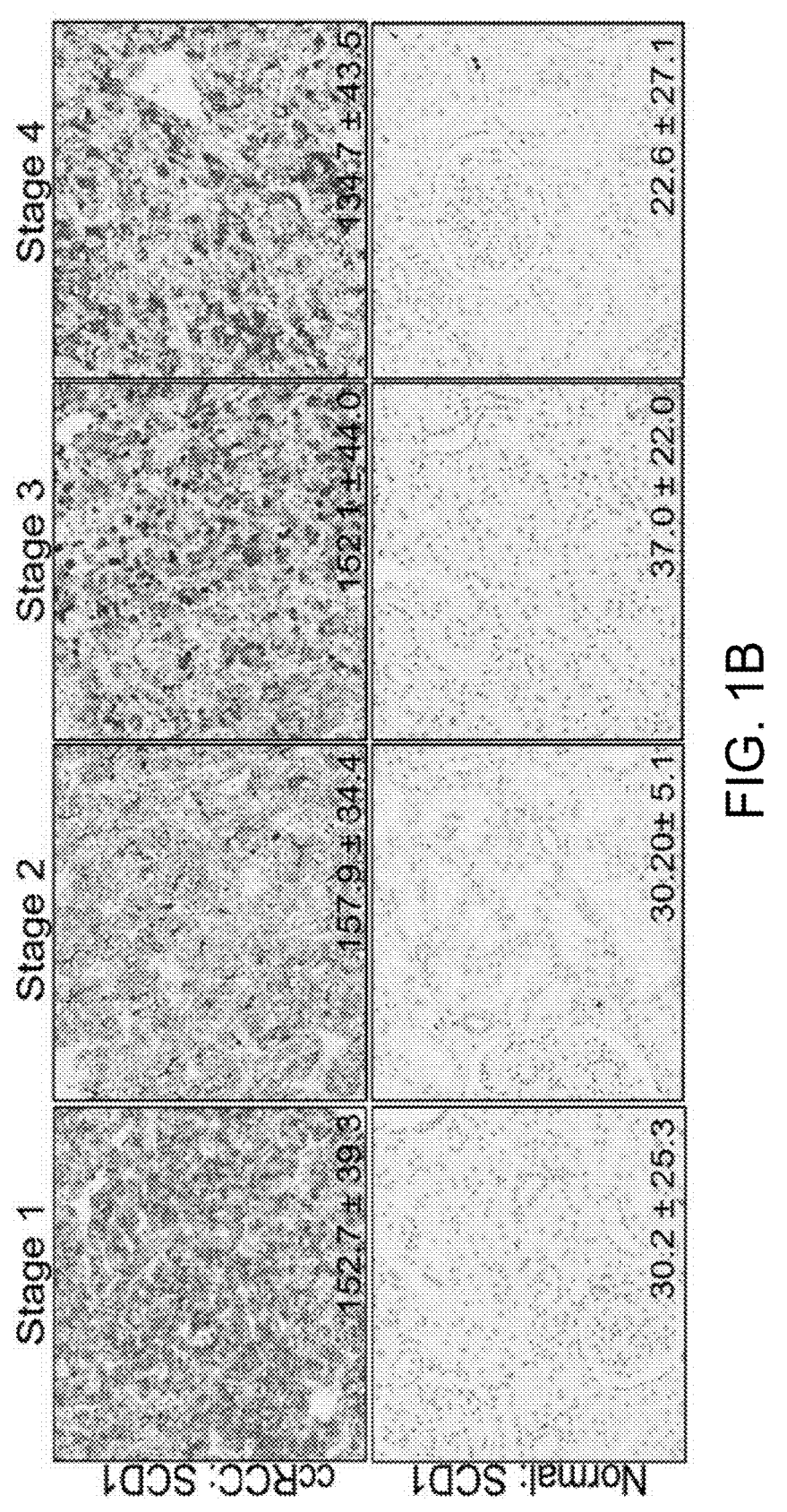

The levels of SCD1 mRNA and SCD1 polypeptide expression also were determined in established ccRCC cell lines and normal renal epithelial cells. SCD1 mRNA levels and SCD1 polypeptide levels were elevated in established ccRCC cell lines when compared to normal renal epithelial cells (FIGS. 1C and 1D). RWV366T is a newly established patient derived ccRCC cell line, whose patient and renal origins were validated by STR analysis and IHC for renal markers (data not shown).

To determine the involvement of SCD1 expression in renal cell carcinoma proliferation, two separate lentiviral constructs were designed to express shRNA molecules having the ability to reduce SCD1 expression. The first lentiviral construct was designed to express an shRNA designated SCD780. The sequence of SCD780 was as follows: 5'-CTACGGCTCTTTCTGATCATT-3' (SEQ ID NO:1). The second lentiviral construct was designed to express an shRNA designated SCD1200. The sequence of SCD1200 was as follows: 5'-CGTCCTTATGACAAGAACATT-3' (SEQ ID NO:2). A non-target lentiviral construct was designed as a control.

Figure 2A:
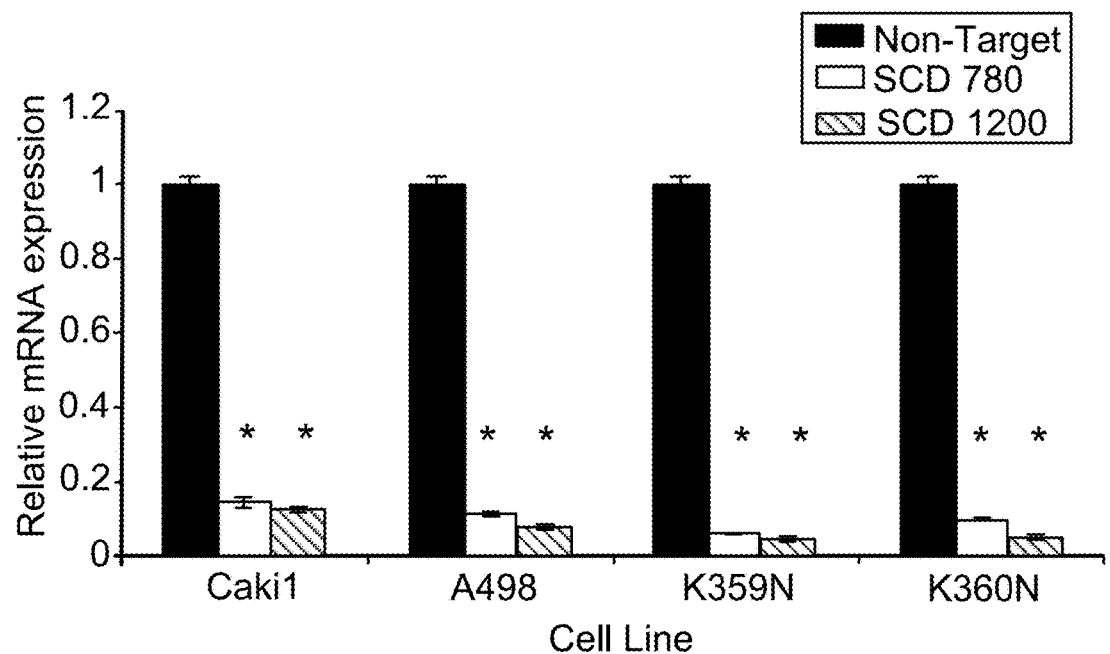
FIGS. 2A and 2D shows the knockdown of SCD1 in ccRCC as shown by decrease in both (A) mRNA and (D) protein expression using two separate lentiviral constructs shSCD780 and shSCD1200.
Figure 2B:
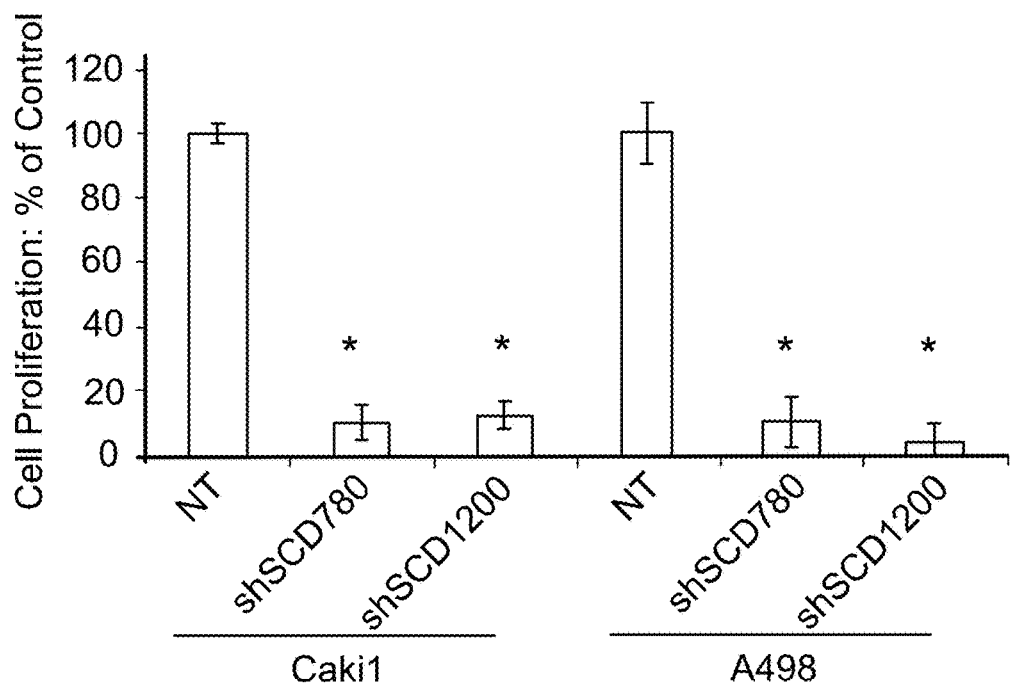
FIGS. 2B and 2C show proliferation in (B) A498 and Caki1 ccRCC cell lines and (C) NRE samples of NT versus shSCD lentiviral infected cells.
Figure 2C:
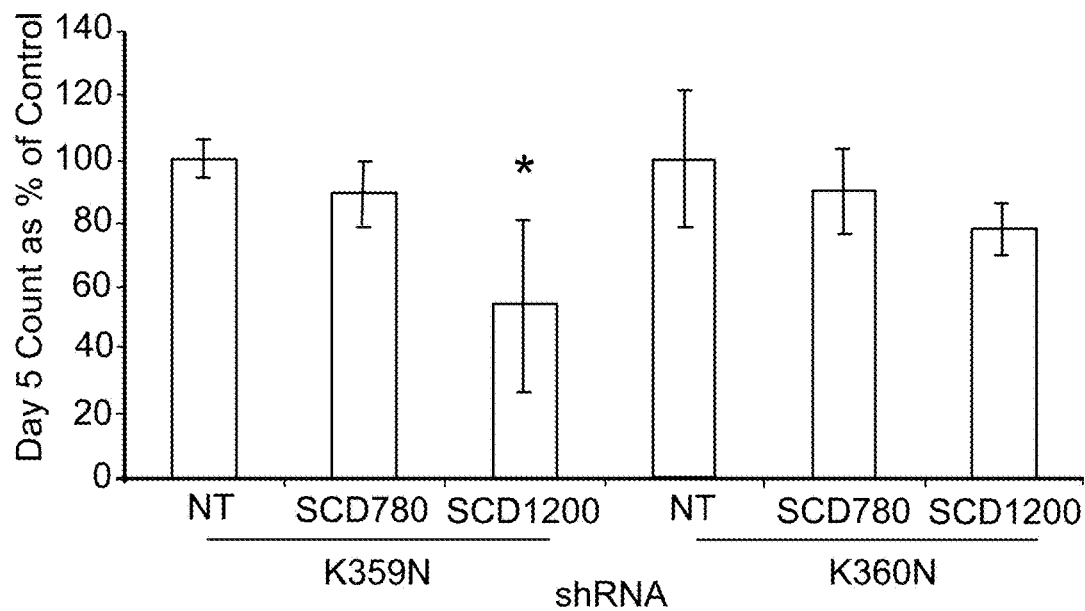
Figure 2D:
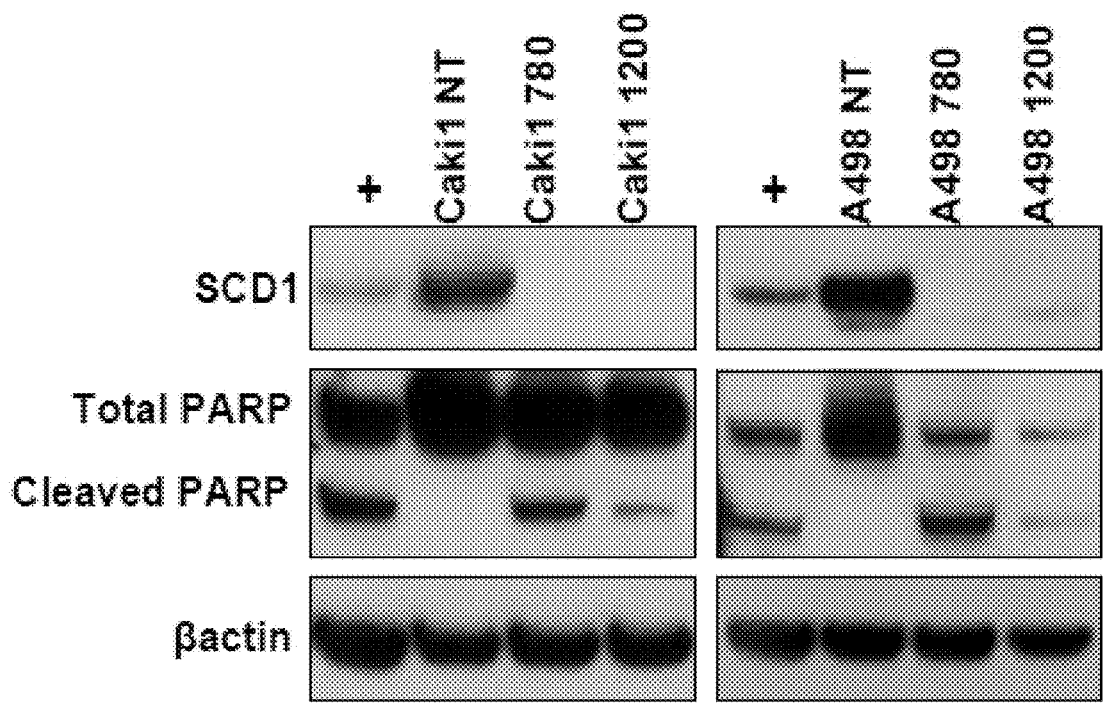

Treatment of established ccRCC cell lines (Caki1 and A498) with lentiviral constructs designed to express SCD780 or SCD1200 resulted in reduced SCD1 mRNA expression levels (FIG. 2A) and reduced SCD1 polypeptide expression levels (FIG. 2D). The reduction in SCD1 expression in ccRCC cells revealed the induction of apoptosis as demonstrated by poly ADP ribose polymerase (PARP) cleavage (FIG. 2D). Treatment of normal renal epithelial cells (K359N and K360N) with lentiviral constructs designed to express SCD780 or SCD1200 resulted in reduced SCD1 mRNA expression levels (FIG. 2A).

A proliferation assay was performed to determine if reduced SCD1 expression preferentially reduced the ability of established ccRCC cell lines to proliferate as compared to normal kidney cells. Treatment of established ccRCC cell lines (Caki1 and A498) with lentiviral constructs designed to express SCD780 or SCD1200 resulted in reduced proliferation as compared to the levels of proliferation observed with normal kidney cells (K359N and K360N) treated with the lentiviral constructs (FIGS. 2B and 2C).

These results demonstrate that inhibitors of SCD1 can be used to reduce the number of ccRCC cells present within a mammal, while having little or no effect on normal kidney cells. These results also demonstrate that loss of SCD1 in ccRCC cells can lead to apoptotic programmed cell death.

Example 2

Oleic Acid Reverses Effects of Decreased SCD1 Expression in Tumor Cells

As oleic acid (OA) is the principle product of SCD1 mediated SFA dehydrogenation, a cell culture stable form of OA conjugated to albumin from bovine serum (OA-BSA) was utilized to perform rescue experimentation in order to confirm that decreased tumor cell growth and induction of cell death was due to lentiviral mediated suppression of SCD1.

Figure 3A:
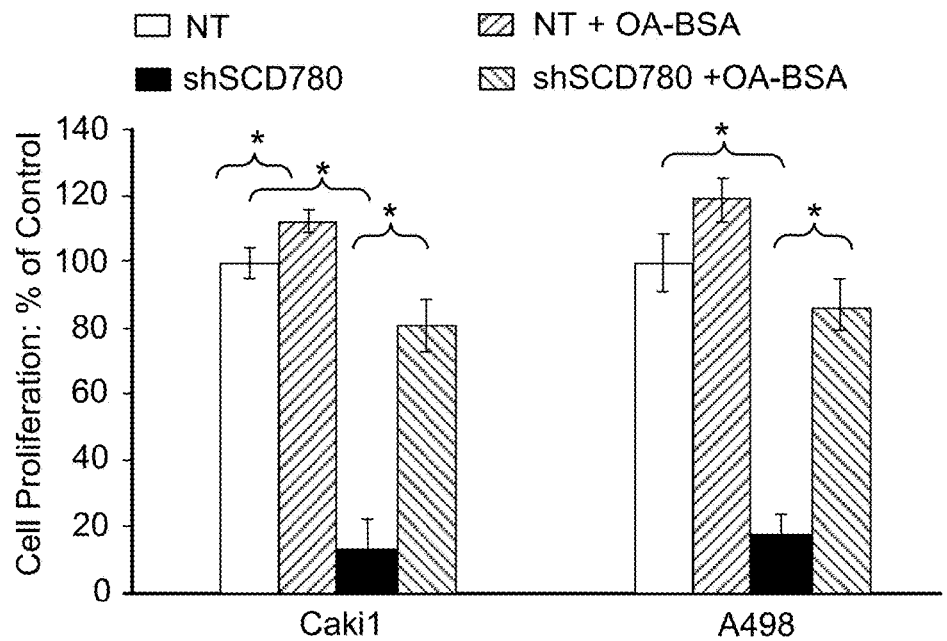
FIGS. 3A-C. Anti-proliferative and apoptotic induction via loss of SCD1 expression can be rescued with addition of oleic acid (OA-BSA).
Figure 3B:
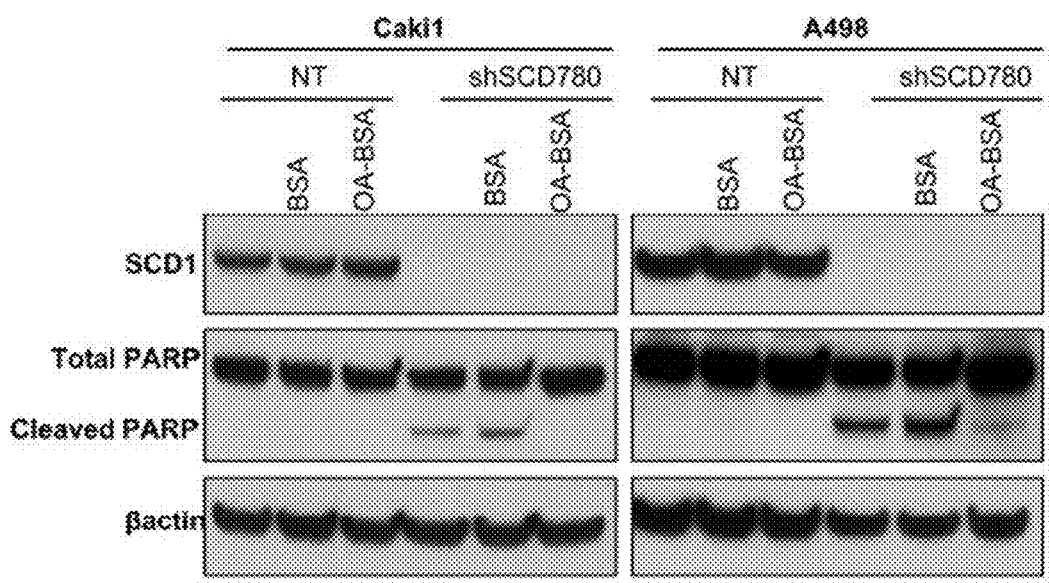
Figure 3C:
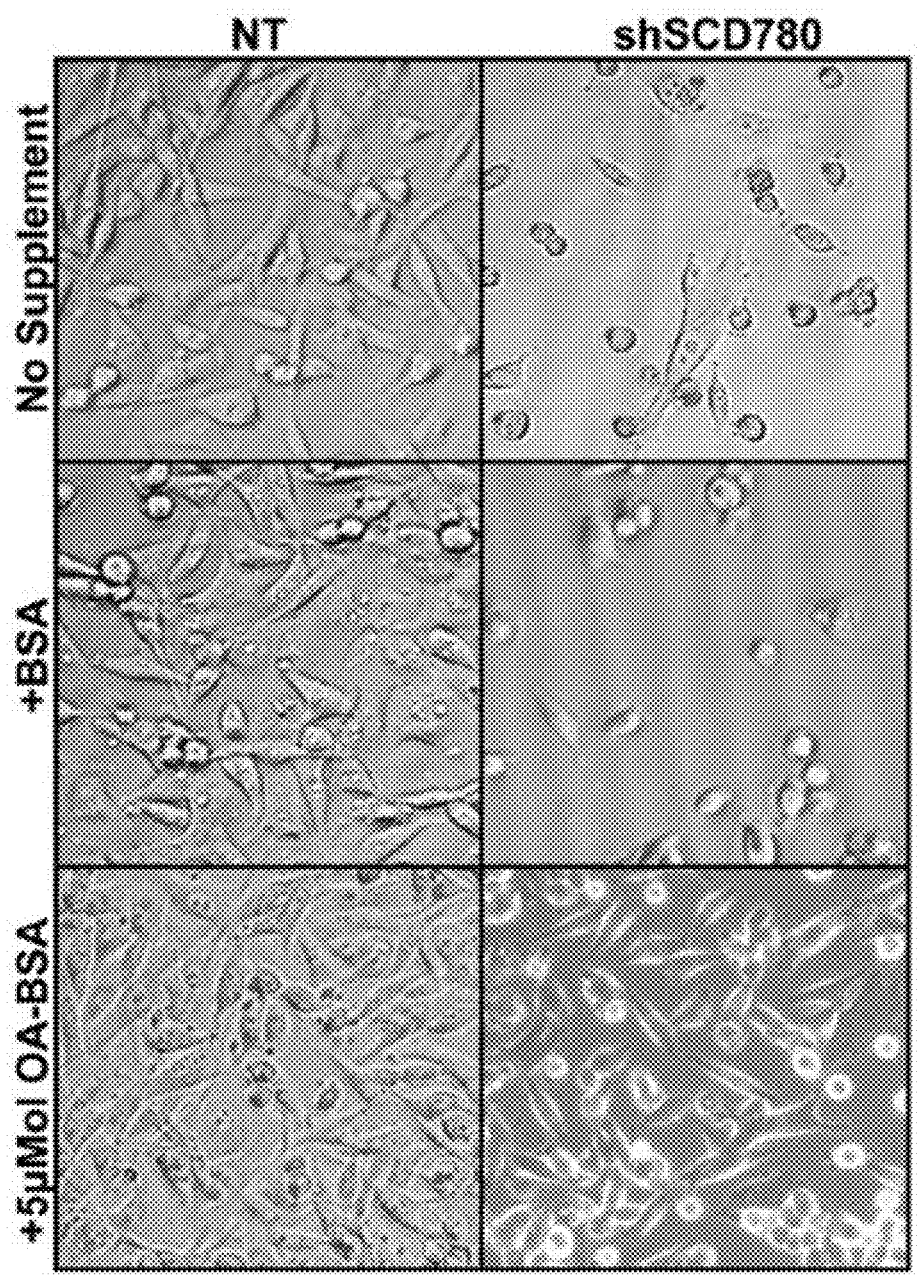

Media alone and BSA supplemented media served as control groups. Proliferation assay of NT control versus shSCD780 infected Caki1 and A498 cells cultured in media with or without OABSA were counted after five days. Both Caki1 and A498 shSCD780 cells exhibited significant decreases in growth when compared to controls; however the addition of OA-BSA rescued the proliferative capacity of these cells to near control rates (FIG. 3A). Notably, addition of OABSA to Caki1 NT cells marginally enhanced proliferation (FIG. 3A). SCD1 knockdown by lentiviral infection was confirmed at the protein level (FIG. 3B). In addition to growth rescue, supplementation with OA-BSA also decreased shSCD780 induced apoptosis as demonstrated by reduction in PARP cleavage shown by western blot (FIG. 3B). Representative phase contrast images of ccRCC cells for each group are shown in FIG. 3C.

Example 3

Small Molecule Inhibition of SCD1 Induces ccRCC Cell Death

Figure 4A:
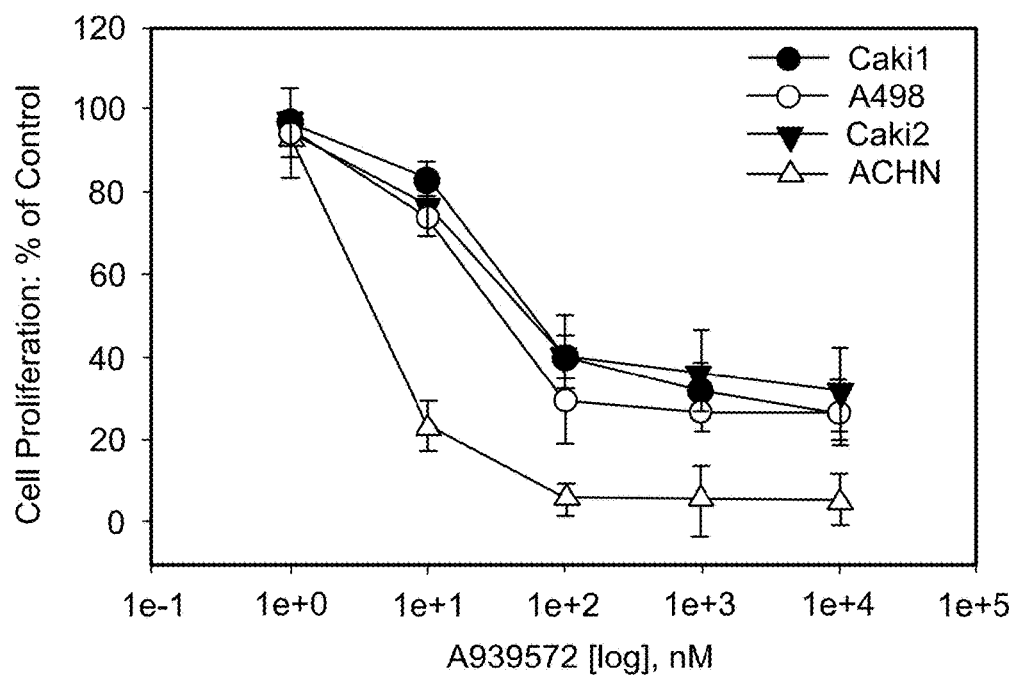
FIGS. 4A-D. Treatment of ccRCC cells with a small molecule SCD1 inhibitor, A939572, inhibits cell growth and induces apoptosis.
Figure 4B:
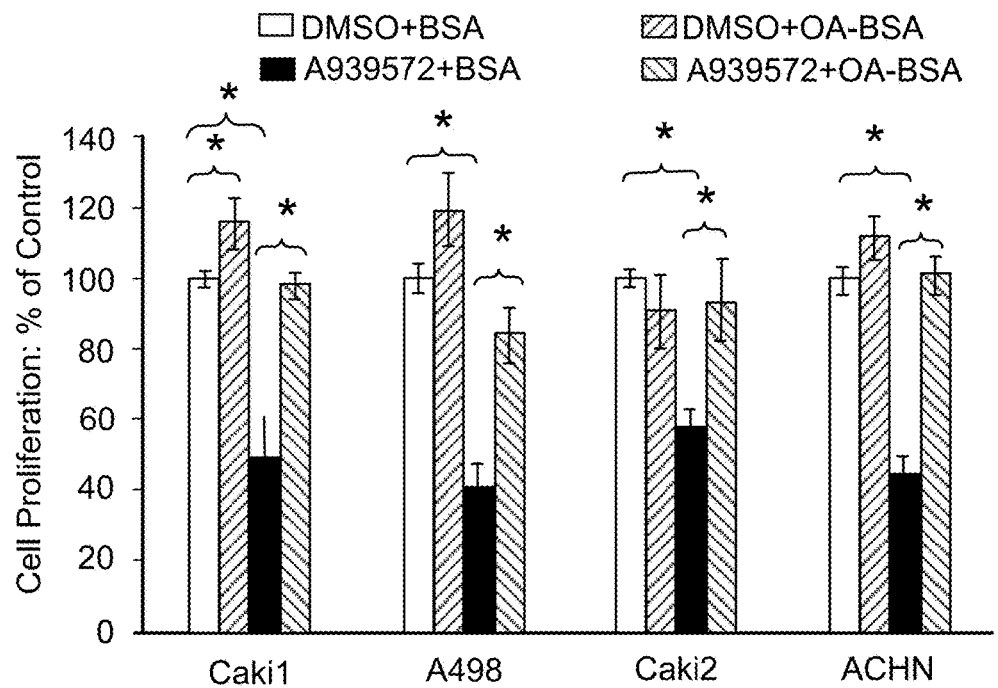
Figure 4C:
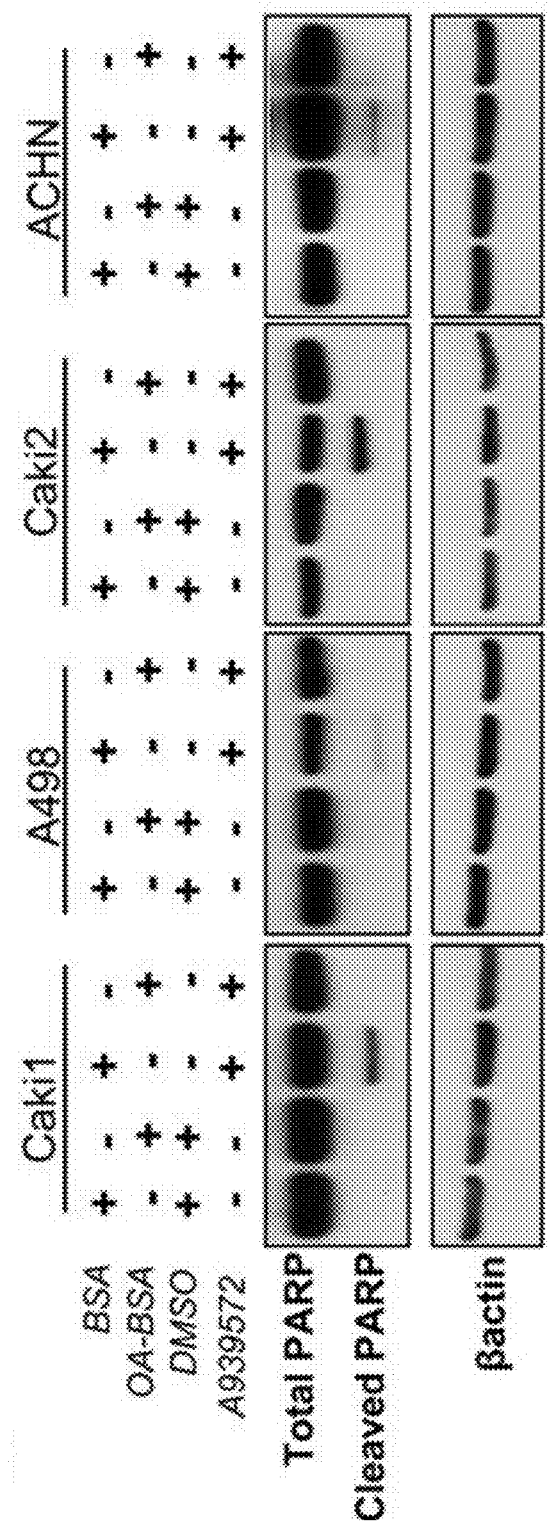
Figure 4D:
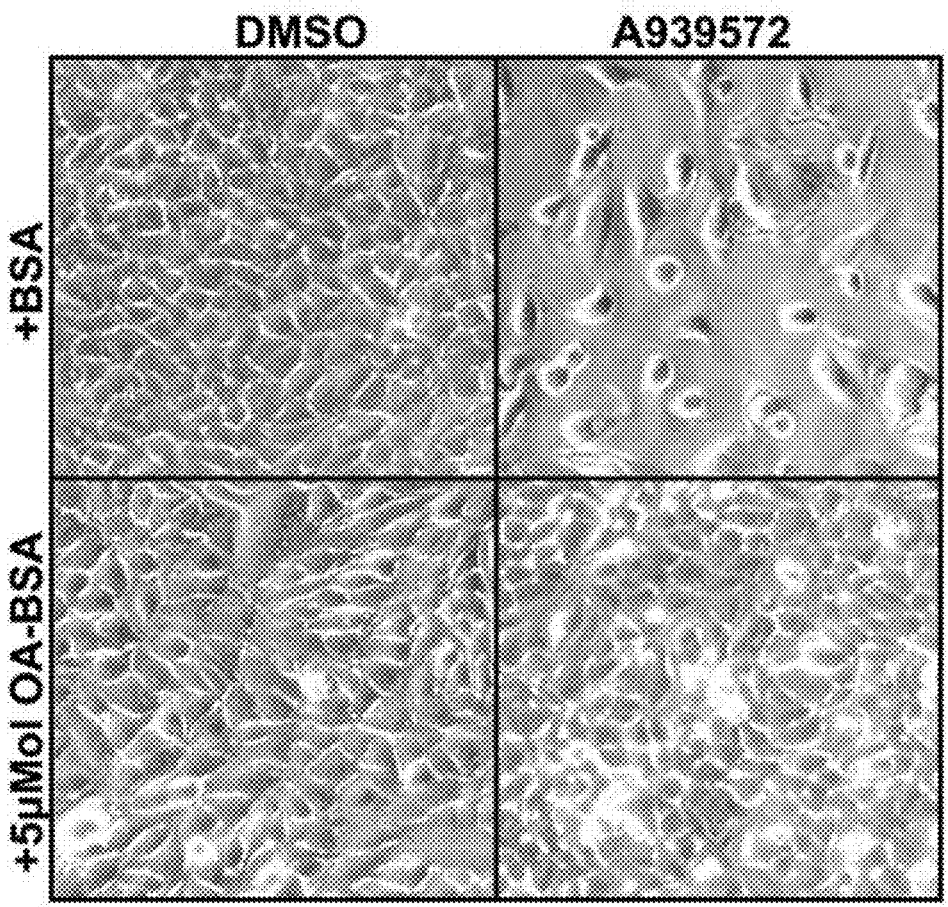

A939572 was dosed out in four ccRCC cell lines Caki1, A498, Caki2, and ACHN, and demonstrated a significant dose-dependent decrease in proliferation at day 5 (IC50s of 65 nM, 50 nM, 65 nM, and 6 nM, respectively) (FIG. 4A). Molecular target specificity was confirmed by addition of OA-BSA to the growth inhibitory assay, with IC50 doses applied to all four cell lines versus DMSO+BSA control. Addition of OA-BSA prevented A939572 mediated growth inhibition which was comparable to control groups in all four cell lines (FIG. 4B). In congruity with previous experimentation examining SCD1 lentiviral knockdown models, A939572 induced apoptosis confirmed by PARP cleavage via western blot analysis in all four cell lines (FIG. 4C). Addition of OA-BSA blocked apoptosis noted by lack of PARP cleavage (FIG. 4C). Representative phase contrast cell images (FIG. 4D) demonstrate marked reduction in confluence of A939572 treated ccRCC cells (day 5), which reflects decreased proliferation and induction of cell death as a result of treatment. OA-BSA supplemented cells display no visible alterations in phenotype. Thus, we have identified a specific small molecule SCD1 inhibitor that induces apoptotic cell death that can be rescued by oleic acid.

Example 4

Treatment of ccRCC Cells with A939572 Induces Endoplasmic Reticulum Stress

In order to determine the mechanism of decreased proliferation and induction of cell death associated with loss of SCD1 activity in ccRCC cells, gene array analysis was performed with Caki1, A498, Caki2, and ACHN ccRCC cells treated for 24 hours with a 75 nM dose of A939572 compared to DMSO control. Gene expression data was analyzed using the Ingenuity® Systems (IPA) program and revealed increased expression of ER stress response genes associated with UPR.

Figure 5A:
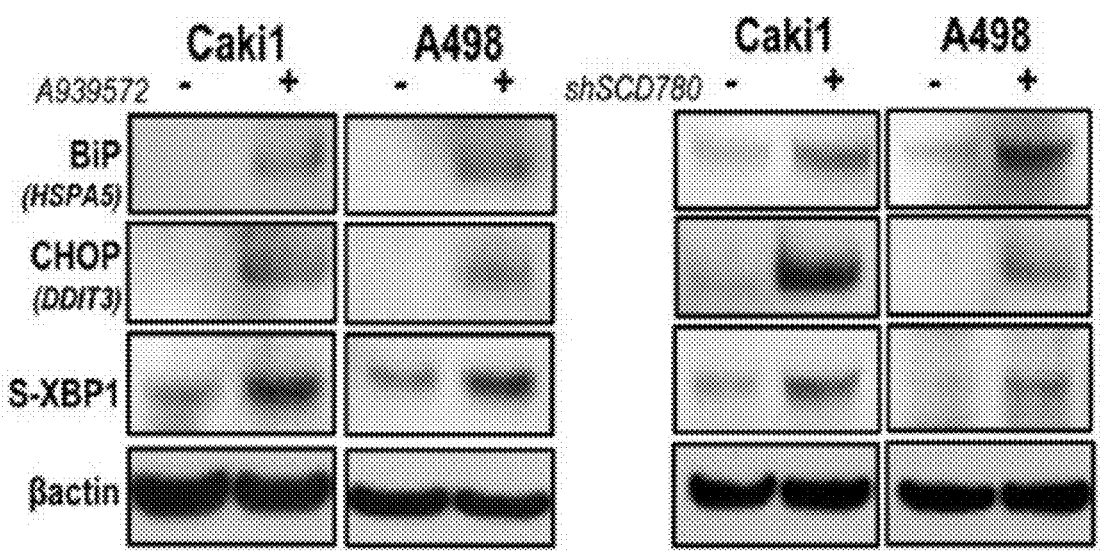
FIGS. 5A-C. Inhibition of SCD1 activity in ccRCC induces cell death mediated by endoplasmic reticulum stress response.

Western blot of Caki1 and A498 cells for protein expression of key ER stress markers including BiP (heat shock 70 kDa protein, GRP78), CHOP (DNA damage inducible transcript 3, DDIT3), and spliced-XBP1 (x-box binding protein 1, s-XBP1) revealed amplified expression in both drug treated (75 nM) and shSCD780 lentiviral knockdown cells after 48 hours (FIG. 5A), confirming induction of ER stress upon loss of SCD1 activity or expression as implicated by the gene array analysis.

Figure 5B:
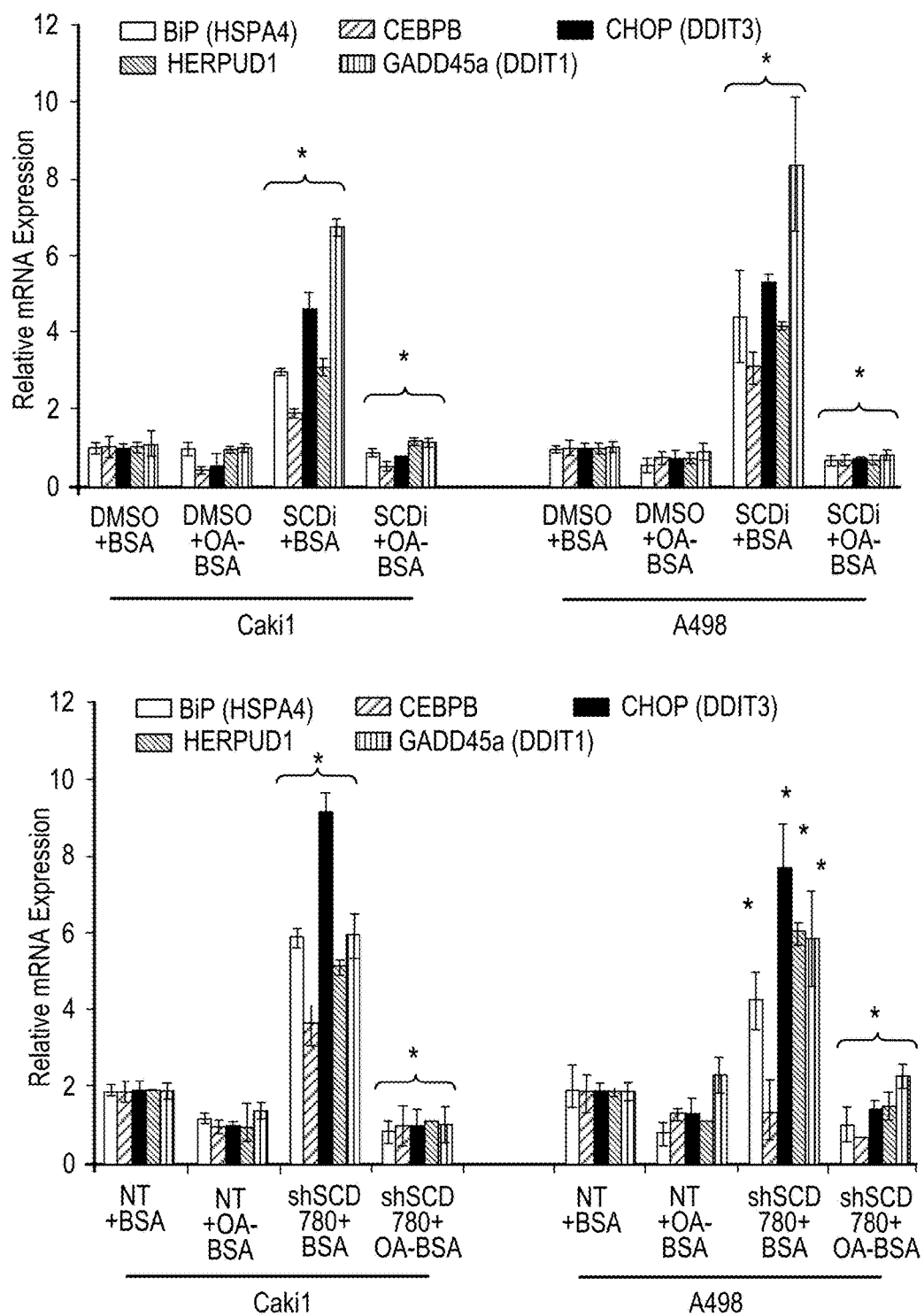

In order to validate the specificity of ER stress induction mediated by both A939572 and shSCD780, rescue assays were performed using OA-BSA in Caki1 and A498 cells qPCR analysis of five ER stress genes identified in the gene array including BiP, CHOP, HERPUD1 (homocysteine-inducible, ER-stress inducible, ubiquitin-like-1), GADD45a (DNA damage inducible transcript 1, DDIT1), and CEBPβ (CCAAT/enhancer binding protein beta) were examined. In A939572 (SCDi) treated Caki1 and A498 cells, all five ER stress related genes were expressed at significantly increased levels compared to DMSO+BSA control, and this elevated expression could be blocked with the addition of OA-BSA (FIG. 5B). In shSCD780 lentiviral infected Caki1 and A498 cells, all of the ER stress genes were significantly induced in the Caki1 shSCD780 sample and 4 of the 5 were significantly induced in the A498 shSCD780 sample. Similar to the drug treated cells, OA-BSA successfully blocked shSCD780 induced expression of the ER stress genes (FIG. 5B).

Figure 5C:
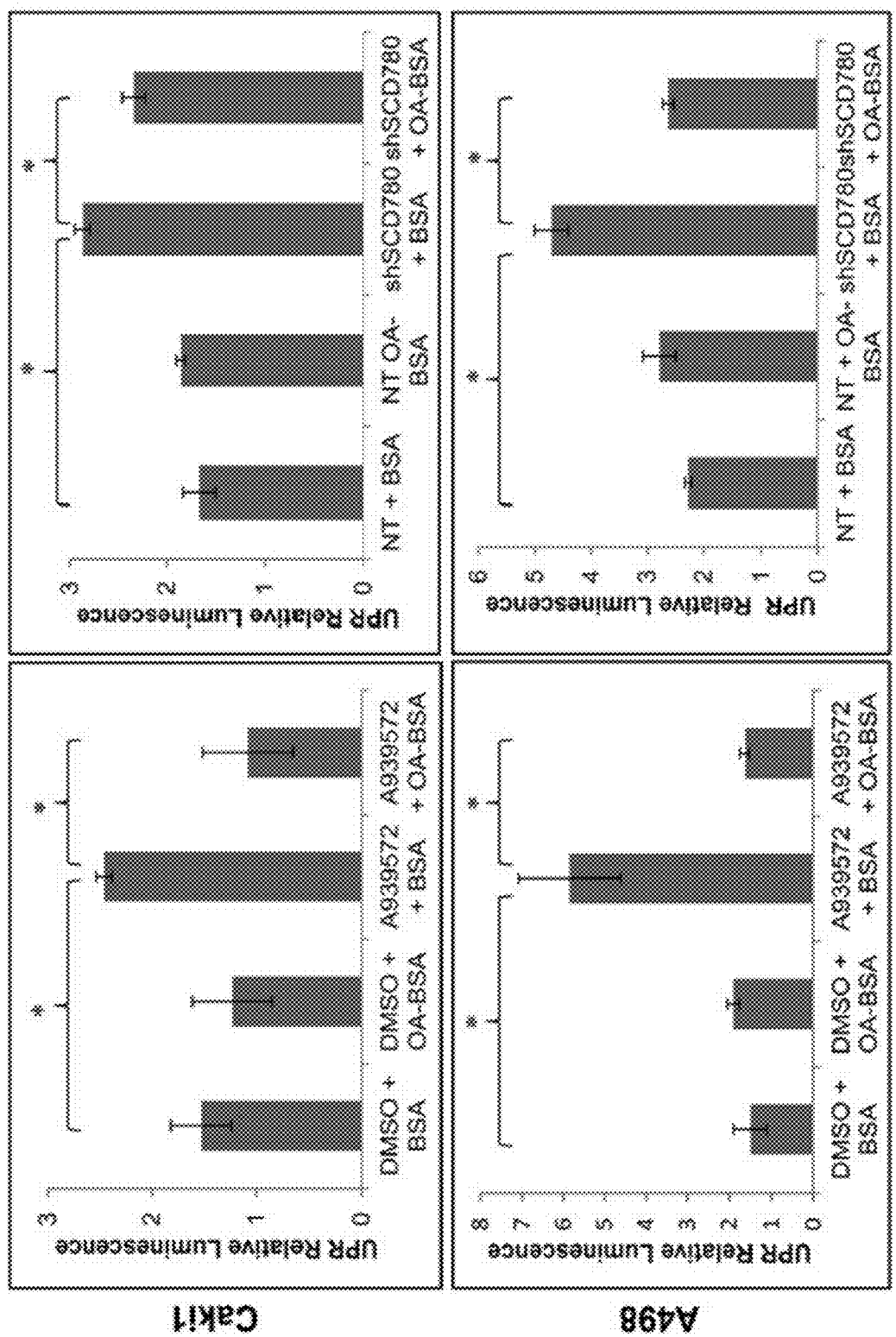

Activating transcription factor 6 (ATF6) is a key bZIP transcription factor that mediates part of the UPR stress response. Upon stress induction ATF6 is proteolytically cleaved into the activated transcription factor allowing it to transcribe several downstream mediators in the ER stress response pathway including XBP1, BiP, HSP90B1 (heat shock protein 90 kDa beta), and CHOP (23). Caki1 and A498 cells transfected with an ATF6 luciferase reporter (p5xATF6-GL3) were treated with a 75 nM dose of A939572 or were infected with shSCD780. Resulting luminescence was measured after 48 hours. Inhibiting SCD1 genetically or pharmacologically resulted in significant enhancement of luciferase activity as compared to DMSO and NT controls with Caki1 A939572+BSA, Caki1 shSCD780+BSA, A498 A939572+BSA, and A498 shSCD780+BSA cells expressing fold change inductions of 1.6, 1.7, 3.8, and 2.0 respectively (FIG. 5C). The addition of OA-BSA significantly reduced reporter activation in response to A939572 and shSCD780, thereby confirming specificity of ATF6 stimulation by loss of SCD1 activity in ccRCC cells. Collectively, these data are indicative that SCD1 inhibition activates the UPR stress response. Tumor cells may therefore be prone to elevated levels of ER stress requiring the induction of protective factors such as SCD1 in order to preserve cell viability. Targeting ER protective constituents presents another potential route for therapeutic intervention not only in ccRCC, but likely in other cancers as well.

Example 5

Combination of A939572 with Temsirolimus Synergistically Enhances Tumor Cell Death In order to target ccRCC using a multifaceted approach, synergy was examined through application of combinatorial treatment utilizing A939572 in congruence with a current FDA approved regimen for ccRCC treatment. These included the TKIs pazopanib and sunitinib, as well as the mTOR inhibitor temsirolimus.

After identifying appropriate cell proliferative dose responses for pazopanib and sunitinib in four ccRCC cell lines including A498, Caki1, Caki2, and ACHN, both TKIs were dosed in combination with A939572 up to approximately the IC50 dose for each drug in the Caki1 and the A498 cell lines. No synergy was noted in either Caki1 or A498 cell proliferative responses with combinatorial treatment. Temsirolimus (Tem) when dosed out in the four ccRCC cell lines yielded a limited reduction in cell proliferation, and no dose response could be determined. Combinatorial treatments were therefore done using a fixed dose of Tem (0.1 nM, 1 nM, and 10 nM) combined with a dose range of A939572 up to the IC50 in Caki1, A498, Caki2 and ACHN cells. Both drugs in combination yielded very strong synergy in all four cell lines as indicated by the combination index (CI) determined using CalcuSyn® based on the Chou- Talalay Method where CI values >1 represent an antagonistic effect and values <1 represent synergy, with lower values signifying enhanced synergy. Colony formation assay of A498 cells grown in soft agar treated with mono and combination doses of 5 nM A939572 and 5 nM Tem reflected synergistic effects observed in combination growth assays performed in 2-D culture and provided the rationale for in vivo analysis of combinatorial therapy.

Figure 6A:
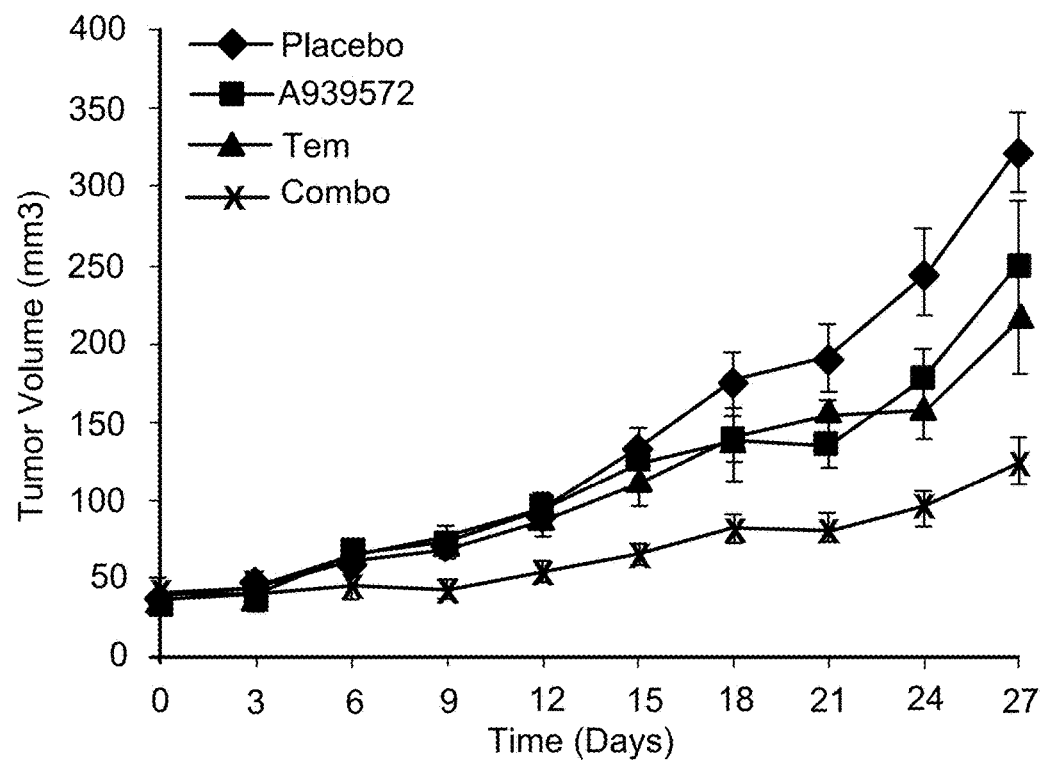

Athymic nude (nu/nu) mice bearing A498 ccRCC xenografts were treated with A939572 and Tem individually or in combination over the course of four weeks, and tumor volume (mm3) was recorded (FIG. 6A). A939572 and Tem monotherapy generated similar growth responses with approximately 20-30% reductions in tumor volume (vs. placebo control) being observed upon study completion, with values reaching statistical significance only within the last week of treatment. The combination group yielded over a 60% decrease in tumor volume (vs. placebo control) by study completion with significant reductions recorded after approximately 1 week of treatment. All of the animals maintained a healthy weight throughout the course of the treatment (FIG. 6A), however those in both the A939572 and the Combo group exhibited increased blinking, and slight mucosal discharge from the eyes after the first week of treatment.

Figure 6C:
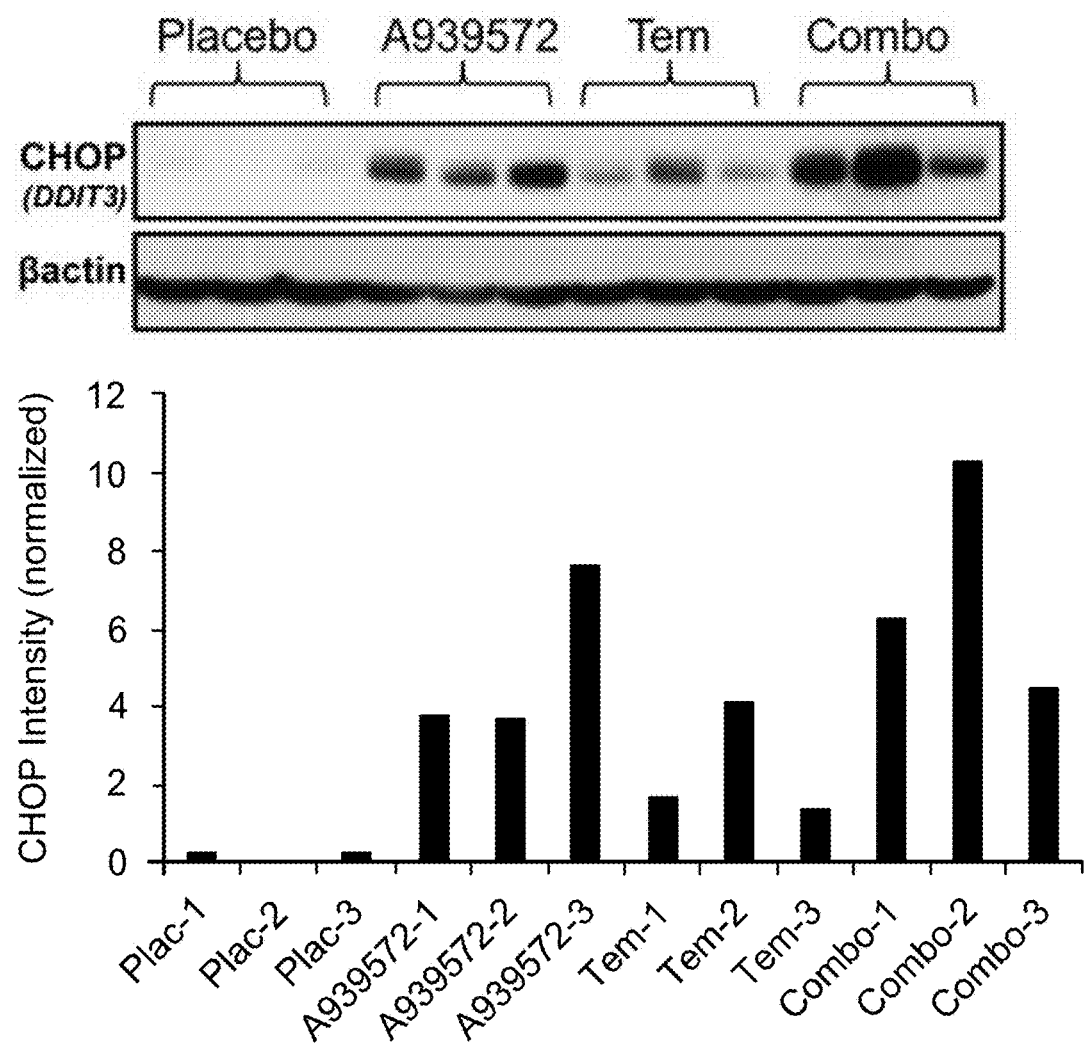
Figure 6D:
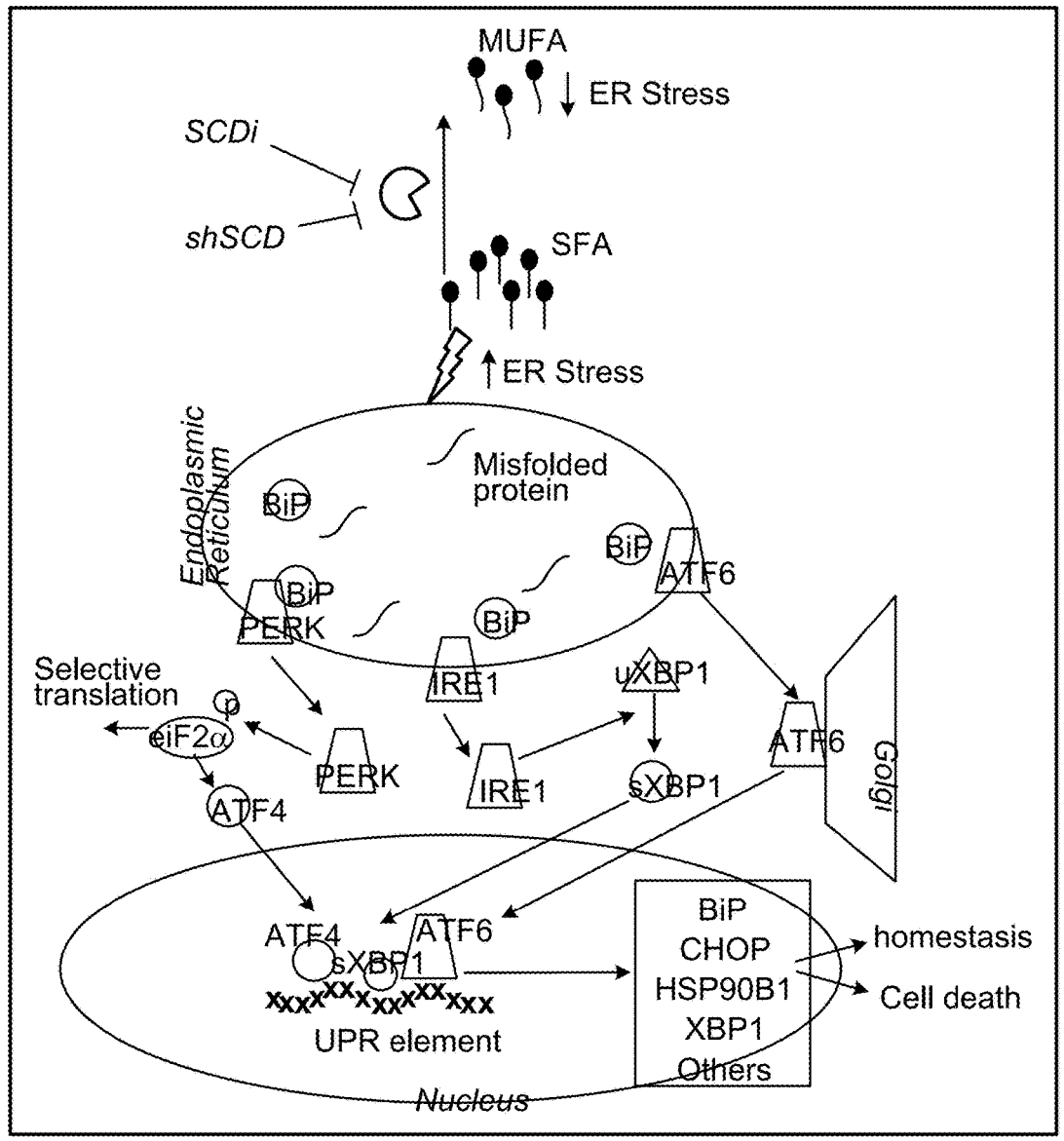

IHC analysis of tumors resected from each treatment group was analyzed for proliferation, angiogenesis, and cell death (FIG. 6B). All treatment groups (A939572, Tem, and Combo) when compared to the placebo control exhibited decreased proliferation as marked by reduction in percent positivity of nuclear Ki67 staining, with the combinatorial group demonstrating the most significant decline. Angiogenesis as examined by intensity of microvessel density demonstrated a slight decrease in both the Tem and the Combo groups; however the cumulative scores were not considered significant. Cell death as examined by cleaved caspase-3 (CC3) demonstrated significant increases in the Combo group when compared to all groups. A moderate increase in cell death was also seen in the A939572 and Tem groups compared to the placebo. Phosphorylated mTOR was inspected as a marker for temsirolimus activity, and decreased expression was confirmed in both the Tem and the Combo groups as compared to the Placebo and A939572 groups. ER stress was examined via western blot of total protein extractions prepared from randomly selected tumor tissue samples representing each treatment group, and resulting quantitative expression was normalized to respective βactin controls. Increased expression of CHOP was confirmed in all samples treated with A939572 (A939572 and Combo) (FIG. 6C) confirming that inhibition of SCD1 in ccRCC contributes to ER stress in vivo. A proposed mechanism is summarized in FIG. 6D. Interestingly, samples in the Tem group also exhibited induction of CHOP, although to a lesser extent when compared to A939572 and Combo groups. Temsirolimus has been previously reported to decrease SCD1 expression in breast cancer cells. Inhibition of mTOR in ccRCC could indirectly mediate ER stress through decrease of SCD1, thereby explaining our observations. No significant increase in CHOP expression was seen in any placebo samples, confirming specificity of ER stress induction as a result of drug treatment.

Example 6

Inhibition of SCD1 Polypeptide in Various Cancer Cell Lines

A number of cancer cell lines were tested to determine whether SCD1 protein expression correlates with growth inhibition of an SCD1 inhibitor in human cancer cell lines.

Pancreatic Cancer

Figure 7D:
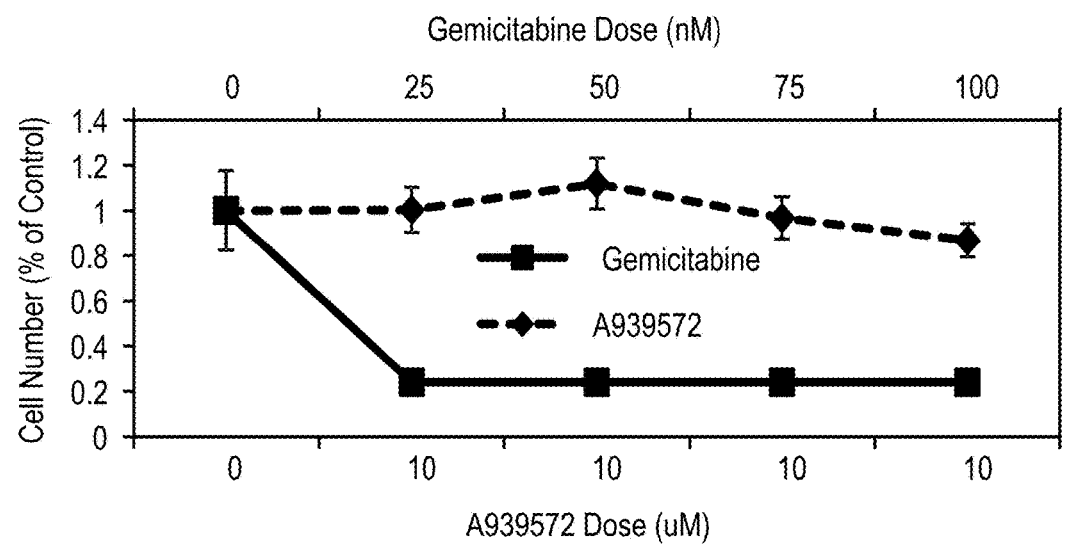
Figure 7E:
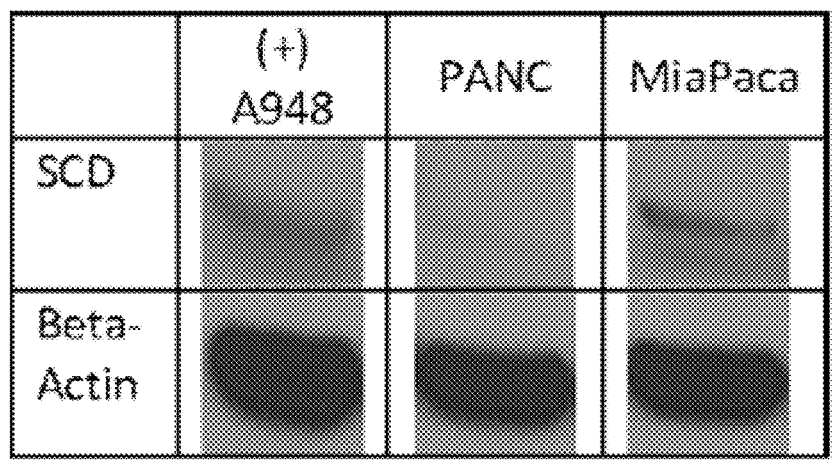
FIG. 7E contains photographs of Western Blot and quantitation of SCD1 and beta-actin expression.

Cells (20,000/ml) were plated in 12 well cell culture plates, allowed to attach and treated with the indicated dose of SCD1 inhibitor (A939753) or standard of care (gemcitabine). Cell number was counted using a Coulter Counter. As show in FIG. 7, the data are expressed as percent of DMSO control. Each value represents triplicates. Western analysis for SCD1 protein expression was performed on each cell line with beta-actin as the loading control. The data indicated that MiaPaca cells express SCD1 and were growth inhibited in a dose dependent fashion while Panc cells expressed very low levels of SCD1 and were growth inhibited at only high levels of SCD1 inhibitor, A939572.

The following cell lines were studied using a similar method as that described above.

Liver Cancer

Figure 8B:
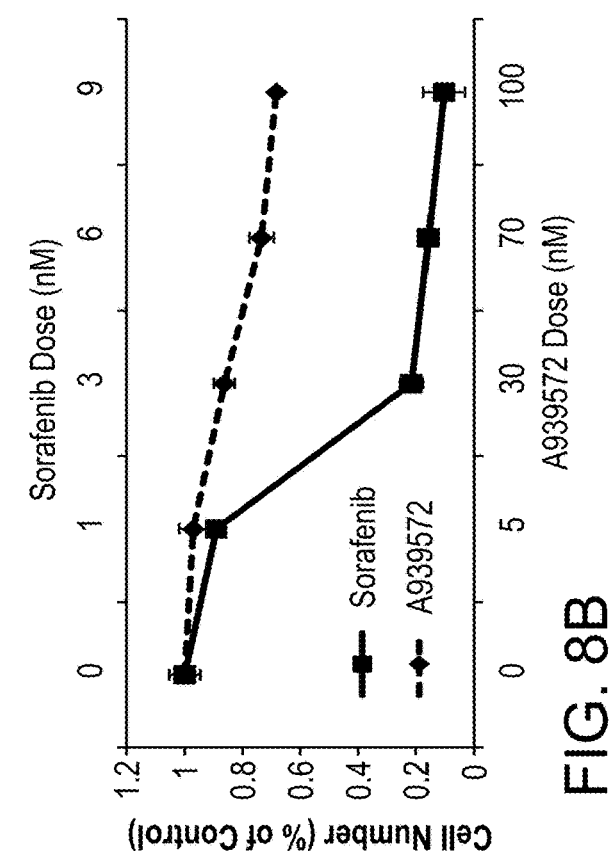
FIGS. 8A-B are line graphs comparing cell number to dose of A939572 or Sorafenib in SNU449 liver cancer cells.
Figure 8A:
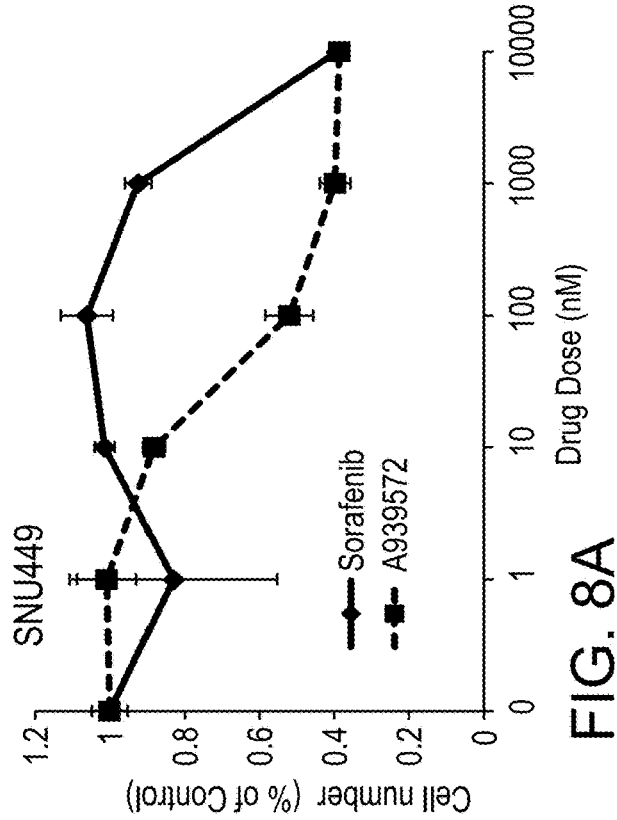
Figure 8C:
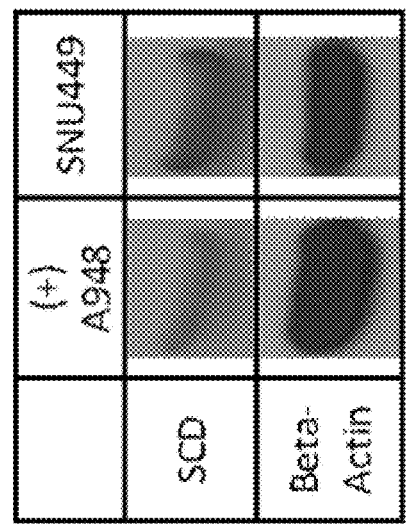
FIG. 8C contains photographs of Western Blot and quantitation of SCD1 and beta-actin expression.

It was found that SNU449 liver cancer cells express SCD1 protein and are growth inhibited in a dose dependent fashion by the SCD1 inhibitor, A939572 (see FIG. 8). An estimated $IC_{50}$ concentration occurred around 100 nM. Sorafenib is FDA approved for liver cancer treatment and is effective between 1-10 micromolar concentrations.

Melanoma

A375 melanoma cells express SCD1 protein and were growth inhibited in a dose dependent fashion by the SCD1 inhibitor, A939572 (see FIG. 9). An estimated IC50 concentration occurred around 50 nM. Mela 11 melanoma cells do not express SCD1 and were not growth inhibited. Standard of care, Temodar, dose responsively inhibits growth in A375 cells but not Mela 11.

Colon Cancer

Caco2 and HT29 colon cancer cells express SCD1 protein and are growth inhibited in a dose dependent fashion by the SCD1 inhibitor, A939572 (see FIG. 10).

Bladder Cancer

T24 and HT1376 bladder cancer cells express SCD1 protein and were growth inhibited in a dose dependent fashion by the SCD1 inhibitor, A939572 (see FIG. 11). The standard of care for bladder cancer, Cisplatin, has minimal growth inhibitory effects on these two cell lines.

Figure 12B:
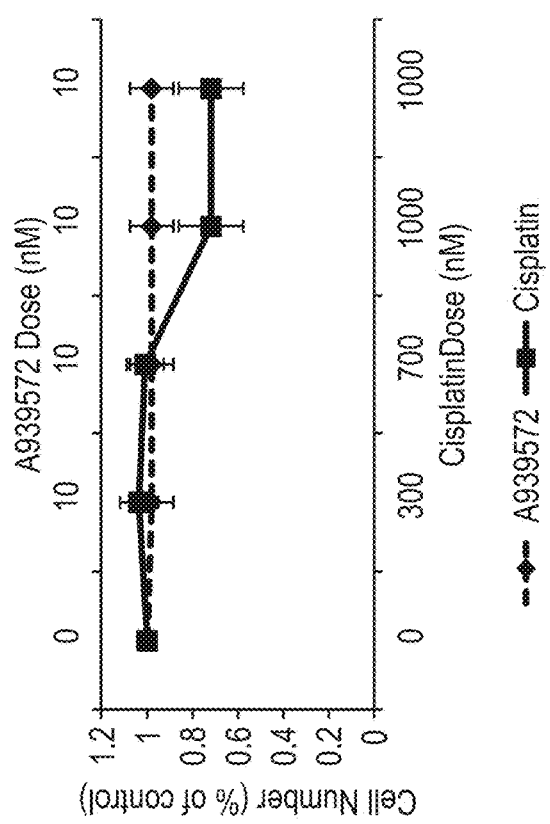
FIGS. 12A-B are line graphs comparing cell number to dose of A939572 or cisplatin in BCJ4T bladder cancer cells.
Figure 12C:
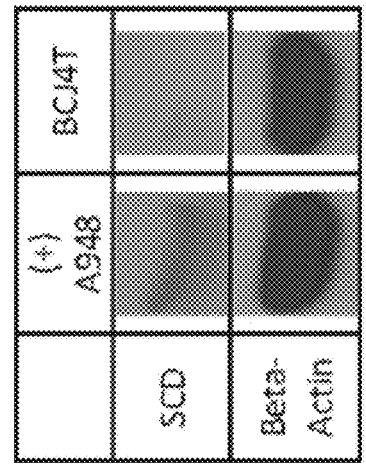
FIG. 12C contains photographs of Western Blot and quantitation of SCD1 and beta-actin expression.
Figure 12A:
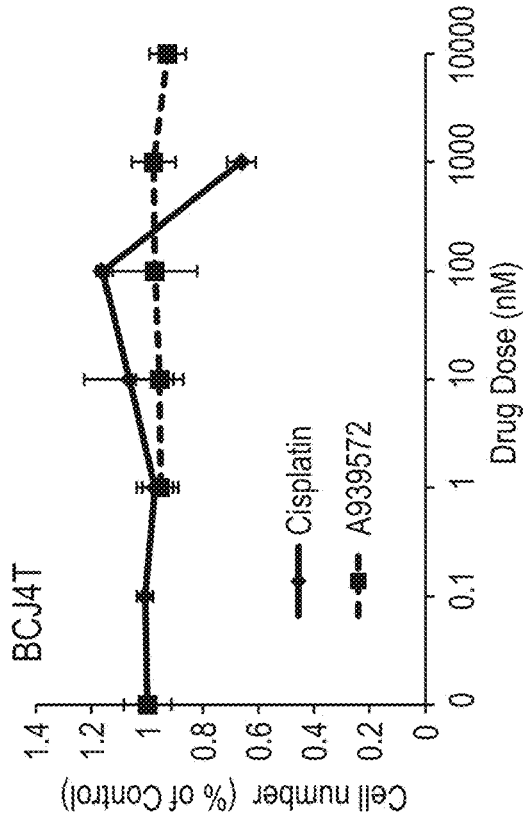

BCJ4T bladder cancer cells do not express SCD1 protein and were not growth inhibited by the SCD1 inhibitor, A939572 (see FIG. 12). The standard of care for bladder cancer, Cisplatin, has minimal growth inhibitory effects on these this cell line.

Anaplastic Thyroid Cancer

Figure 13C:
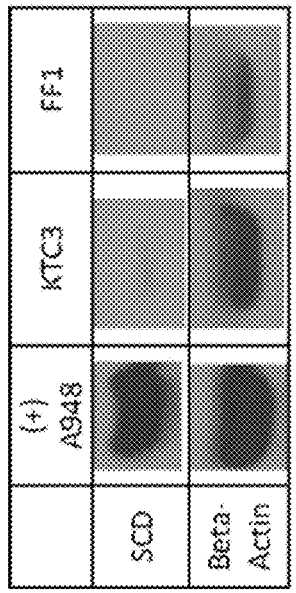
FIG. 13C contains photographs of Western Blot and quantitation of SCD1 and beta-actin expression.
Figure 13A:
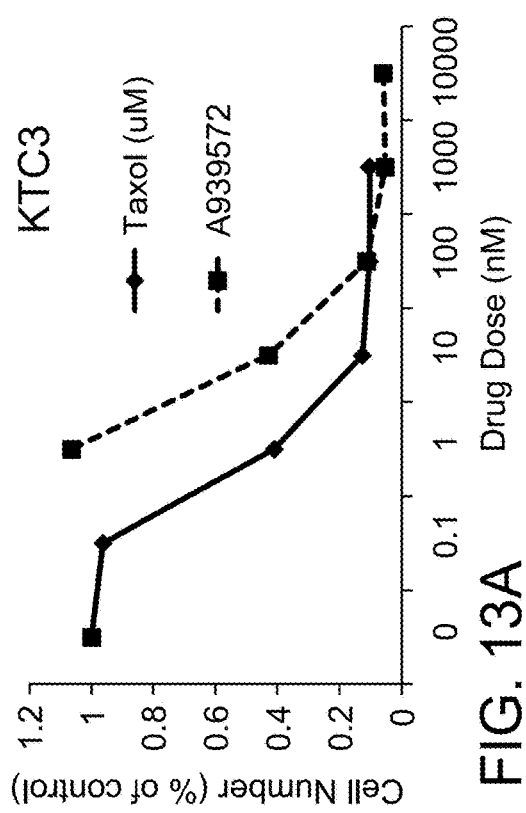
FIGS. 13A-B are line graphs comparing cell number to dose of A939572 or Taxol in KTC3 and FF1 anaplastic thyroid cancer cells.
Figure 13B:
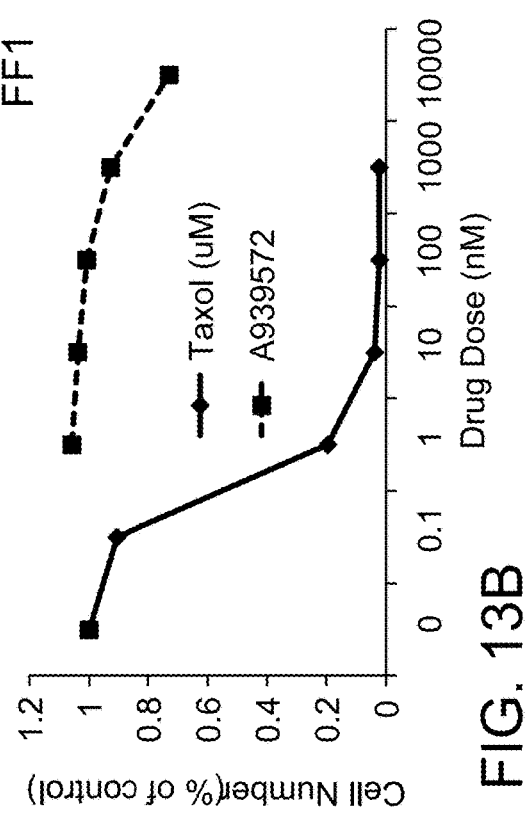

KTC3 thyroid cancer cells express SCD1 protein and were growth inhibited in a dose dependent fashion by the SCD1 inhibitor, A939572 (see FIG. 13). Taxol is growth inhibitory in KTC3 cells but has minimal growth inhibitory effects on FF1 cells.

Lung Cancer

A549 nonsmall cell lung cancer cells express SCD1 protein and were growth inhibited in a dose dependent fashion by the SCD1 inhibitor, A939572 while Calu-1 lung cancer cells do not express SCD1 and are not growth inhibited by A939572 (see FIG. 14). Taxol is growth inhibitory in A549 but was not tested in Calu-1 cells.

Ovarian Cancer

OVCA420 and HOV TAX2 ovarian cancer cells express SCD1 protein and were growth inhibited in a dose dependent fashion by the SCD1 inhibitor, A939572 while Calu-1 lung cancer cells do not express SCD1 and were not growth inhibited by A939572 (see FIG. 15). Taxol is growth inhibitory in HOV Tax2 cells but was not tested in OVCA420 cells.

Breast Cancer

Figure 16A:
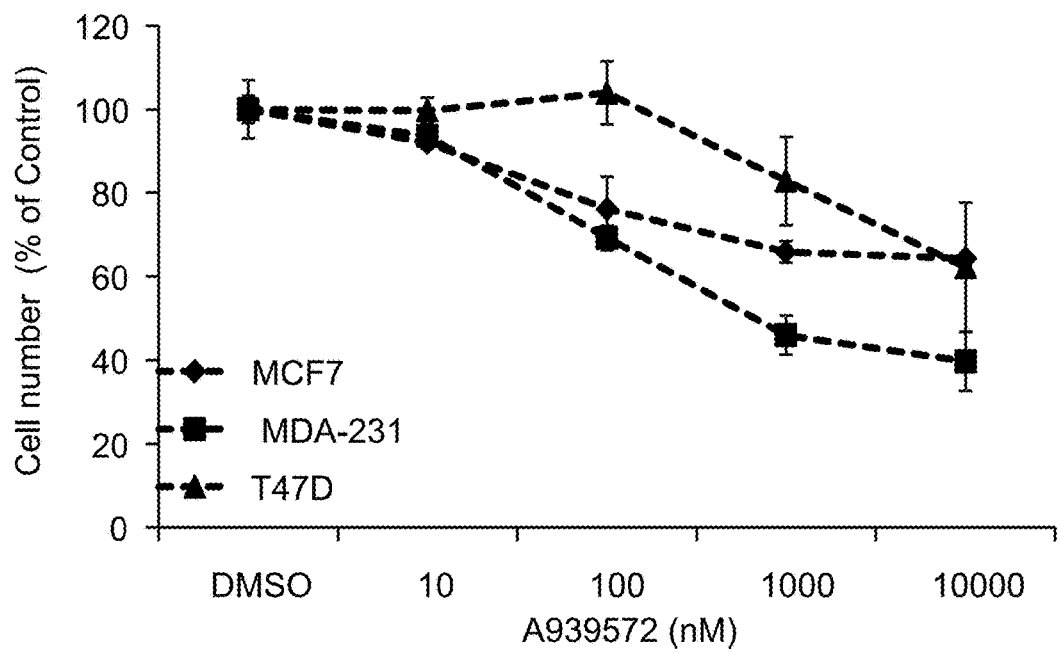
FIG. 16A is a line graph comparing cell number to dose of A939572 in MCF-7 (ER+/PR+), MDA-231 (triple negative) and T47D (PR+) breast cancer cells.
Figure 16B:
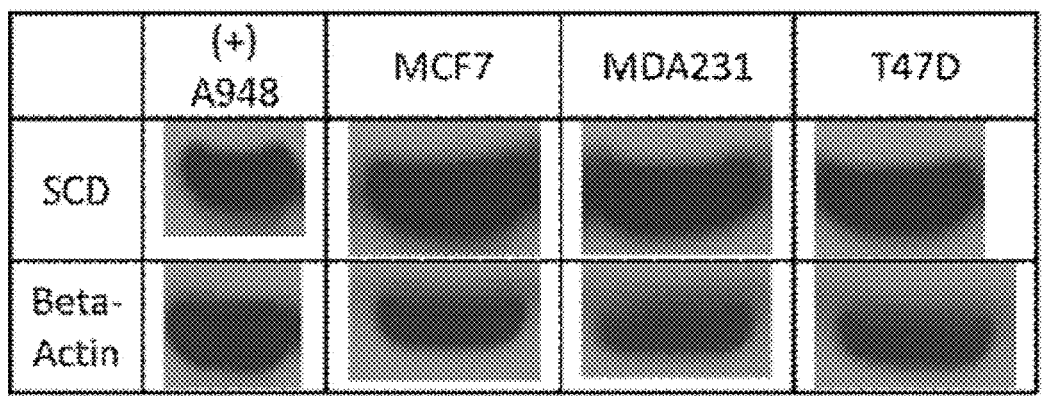
FIG. 16B contains photographs of Western Blot and quantitation of SCD1 and beta-actin expression.

MCF-7 (ER+/PR+), MDA-231 (triple negative) and T47D (PR+) breast cancer cells express SCD1 protein and were growth inhibited in a dose dependent fashion by the SCD1 inhibitor, A939572 (see FIG. 16).

Prostate Cancer

Figure 17A:
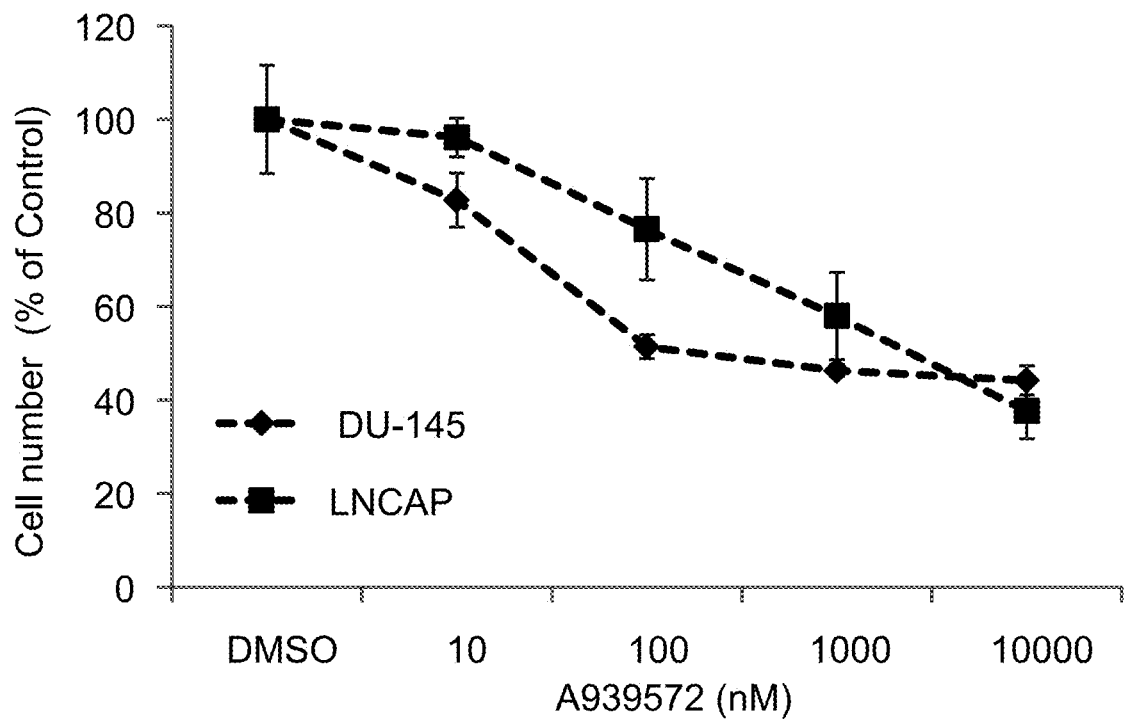
FIG. 17A is a line graph comparing cell number to dose of A939572 in DU-145 prostate cancer cells.
Figure 17B:
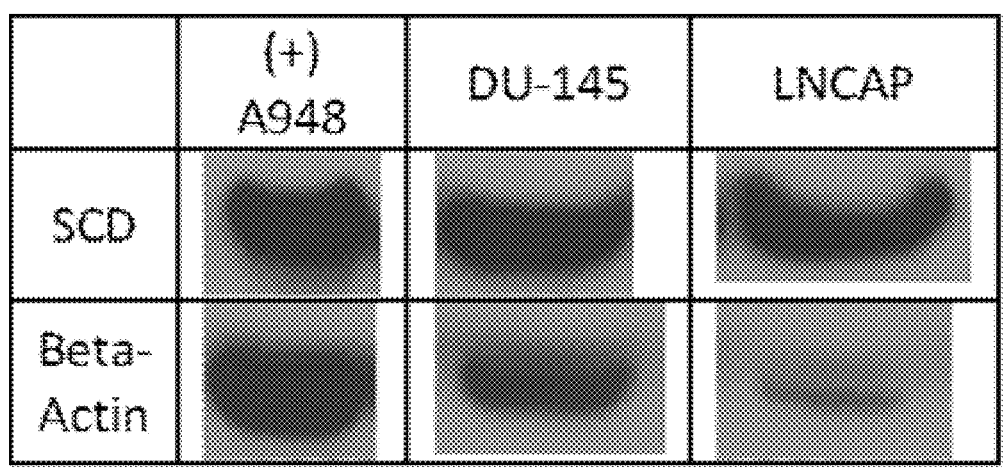
FIG. 17B contains photographs of Western Blot and quantitation of SCD1 and beta-actin expression.
Figure 20:
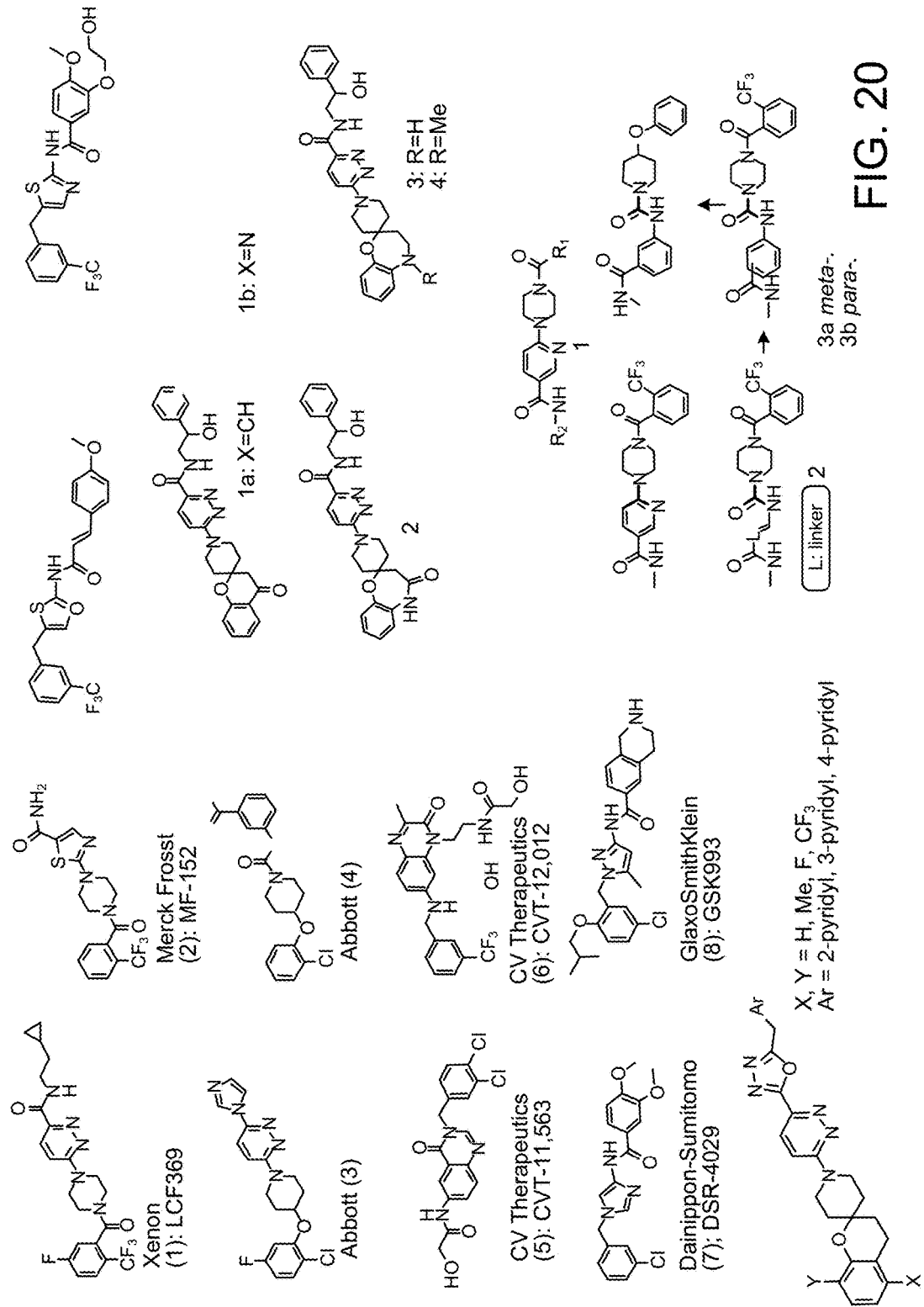

DU-145 and LNCAP prostate cancer cells express SCD1 protein and were growth inhibited in a dose dependent fashion by the SCD1 inhibitor, A939572 (see FIG. 17).

Quantitation (Relative) of SCD1 Protein Expression in Different Cancer Cell Lines As shown in FIG. 18, Western analysis was performed on SCD1 and beta actin. Quantitation was performed by first normalizing to each respective beta-actin followed by normalization to A498 control. SNU449 cells appeared to have the highest SCD1 protein expression while BCJ4, Mela11 and PANC had the lowest protein levels. Protein levels appear to correlate with growth inhibition of the SCD1 inhibitor.

As shown in FIG. 19, Western analysis was also performed on SCD1 and beta actin. Quantitation was performed by first normalizing to each respective beta-actin followed by normalization to A498 control. LN Cap cells appeared to have the highest SCD1 protein expression while Calu1, FF1 and KTC3 cells had the lowest protein levels. Protein levels appear to correlate with growth inhibition of the SCD1 inhibitor.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing the number of cancer cells within a mammal in need thereof, wherein the method comprises administering, to the mammal, an inhibitor of an SCD1 polypeptide under conditions wherein the number of viable cancer cells present within the mammal is reduced, wherein the cancer cells are selected from the group consisting of thyroid cancer cells, melanoma cells, ovarian cancer cells, pancreatic cancer cells, renal cancer cells, and bladder cancer cells.

2. The method of claim 1, wherein the cancer cells are selected from the group consisting of: anaplastic thyroid carcinoma cells, malignant melanoma cells, epithelial ovarian tumor cells, pancreatic ductal adenocarcinoma cells, clear cell renal cell carcinoma, and human urothelial bladder cancer cells.

3. The method of claim 2, wherein the cancer cells are anaplastic thyroid carcinoma cells.

4. The method of claim 2, wherein the cancer cells are malignant melanoma cells.

5. The method of claim 2, wherein the cancer cells are epithelial ovarian tumor cells.

6. The method of claim 2, wherein the cancer cells are pancreatic ductal adenocarcinoma cells.

7. The method of claim 2, wherein the cancer cells are clear cell renal cell carcinoma cells.

8. The method of claim 2, wherein the cancer cells are human urothelial bladder cancer cells.

9. The method of claim 2, wherein the mammal is a human.

10. The method of claim 2, wherein the administration is an intratumoral, oral, intraperitoneal, intramuscular, or intravenous administration.

11. The method of claim 2, wherein the inhibitor is A939572, MK-8245, CVT-11127, MF-152, MF-438, or HYR-061.

12. A method for reducing the number of cancer cells within a mammal in need thereof, wherein the method comprises administering, to the mammal, a composition under conditions wherein the number of cancer cells present within the mammal is reduced, wherein the composition comprises the ability to reduce SCD1 mRNA expression or SCD1 polypeptide expression, wherein the cancer cells are selected from the group consisting of thyroid cancer cells, melanoma cells, ovarian cancer cells, pancreatic cancer cells, renal cancer cells, and bladder cancer cells.

13. The method of claim 12, wherein the cancer cells are selected from the group consisting of: anaplastic thyroid carcinoma cells, malignant melanoma cells, epithelial ovarian tumor cells, pancreatic ductal adenocarcinoma cells, clear cell renal cell carcinoma, and human urothelial bladder cancer cells.

14. The method of claim 13, wherein the cancer cells are anaplastic thyroid carcinoma cells.

15. The method of claim 13, wherein the cancer cells are malignant melanoma cells.

16. The method of claim 13, wherein the cancer cells are epithelial ovarian tumor cells.

17. The method of claim 13, wherein the cancer cells are pancreatic ductal adenocarcinoma cells.

18. The method of claim 13, wherein the cancer cells are clear cell renal cell carcinoma cells.

19. The method of claim 13, wherein the cancer cells are human urothelial bladder cancer cells.

20. The method of claim 12, wherein the mammal is a human.

21. The method of claim 12, wherein the administration is an intratumoral, oral, intraperitoneal, intramuscular, or intravenous administration.

22. The method of claim 12, wherein the composition comprises a nucleic acid construct having the ability to express a shRNA directed against SCD1 nucleic acid.

* * * * *

UNITED STATES PATENT AND TRADEMARK OFFICE
CERTIFICATE OF CORRECTION

PATENT NO. : 10,160,972 B2  
APPLICATION NO. : 15/692491  
DATED : December 25, 2018  
INVENTOR(S) : John A. Copland, III, Laura Ann Marlow and Christina Von Roemeling Page 1 of 1

It is certified that error appears in the above-identified patent and that said Letters Patent is hereby corrected as shown below:

On the Title Page

Column 2 (Other Publications), Line 11, delete "showNCT00790556?" and insert -- show/NCT00790556? --;

Column 2 (Other Publications), Line 13, delete "fmm" and insert -- from --;

In the Claims

Column 17, Line 42, Claim 1, delete "SCD1polypeptide" and insert -- SCD1 polypeptide --;

Column 18, Line 24, Claim 12, delete "SCD1mRNA" and insert -- SCD1 mRNA --;

Column 18, Line 54, Claim 22, delete "SCD1nucleic" and insert -- SCD1 nucleic --.

Signed and Sealed this  
Seventh Day of July, 2020

Andrei Iancu  
*Director of the United States Patent and Trademark Office*